United States Patent
Kloss

(10) Patent No.: US 10,245,152 B2
(45) Date of Patent: Apr. 2, 2019

(54) SURGICAL IMPLANT

(75) Inventor: Henning Kloss, Ennetburgen (CH)

(73) Assignee: Privelop-Spine AG, Stans (CH)

( * ) Notice: Subject to any disclaimer, the term of this patent is extended or adjusted under 35 U.S.C. 154(b) by 299 days.

(21) Appl. No.: 13/811,438

(22) PCT Filed: Jul. 25, 2011

(86) PCT No.: PCT/EP2011/003715
§ 371 (c)(1),
(2), (4) Date: Jan. 22, 2013

(87) PCT Pub. No.: WO2012/010327
PCT Pub. Date: Jan. 26, 2012

(65) Prior Publication Data
US 2013/0116793 A1  May 9, 2013

(30) Foreign Application Priority Data

Mar. 20, 2011 (DE) .......................... 10 2011 014 809

(51) Int. Cl.
*A61B 17/44* (2006.01)
*A61F 2/44* (2006.01)
(Continued)

(52) U.S. Cl.
CPC ............ *A61F 2/442* (2013.01); *A61F 2/4455* (2013.01); *A61F 2/30965* (2013.01);
(Continued)

(58) Field of Classification Search
CPC ...... A61F 2/4455; A61F 2/446; A61F 2/4465; A61F 2/447; A61F 2/30767;
(Continued)

(56) References Cited

U.S. PATENT DOCUMENTS 4,961,740 A * 10/1990 Ray et al. .................... 606/247
5,348,788 A    9/1994 White
(Continued)

FOREIGN PATENT DOCUMENTS

DE  202006015415 U1  11/2006
EP       0621018 A1 * 10/1994  ........... A61C 8/0012
(Continued)

OTHER PUBLICATIONS

Bartolo, Gaspar; "Metal filled resin for stereolithography metal part" CIRP Annals—Manufacturing Technology, 2008, 57, 235-238, http://www.sciencedirect.com/science/article/pii/S0007850608000942.*

(Continued)

*Primary Examiner* — Matthew J Lawson
*Assistant Examiner* — Amy R Sipp
(74) *Attorney, Agent, or Firm* — Knobbe Martens Oslon & Bear, LLP

(57) ABSTRACT

The present invention is directed to a surgical implant for the fusion of two adjacent vertebrae with an upper plane for contacting an upper vertebral body and a lower plane for contacting a lower vertebral body and a tubular structure, wherein the tubular structure is formed by a plurality of tubes running from the upper plane to the lower plane and in substantially horizontal direction throughout one side of the surgical implant straight to the opposite side of the surgical implant. This tubular structure has the advantage that the formation and ingrowth of new bone is promoted and advantaged and that the degree of formation and ingrowth of new bone is detectable by X-ray measurements.

33 Claims, 10 Drawing Sheets

(51) Int. Cl.
*A61F 2/30* (2006.01)
*A61F 2/28* (2006.01)

(52) U.S. Cl.
CPC ..... *A61F 2/4465* (2013.01); *A61F 2002/2817* (2013.01); *A61F 2002/3008* (2013.01); *A61F 2002/30062* (2013.01); *A61F 2002/3092* (2013.01); *A61F 2002/30133* (2013.01); *A61F 2002/30143* (2013.01); *A61F 2002/30146* (2013.01); *A61F 2002/30149* (2013.01); *A61F 2002/30583* (2013.01); *A61F 2002/30617* (2013.01); *A61F 2002/30677* (2013.01); *A61F 2002/4475* (2013.01); *A61F 2310/00017* (2013.01); *A61F 2310/00023* (2013.01); *A61F 2310/00029* (2013.01); *A61F 2310/00089* (2013.01); *A61F 2310/00095* (2013.01); *A61F 2310/00101* (2013.01); *A61F 2310/00125* (2013.01); *A61F 2310/00137* (2013.01); *A61F 2310/00149* (2013.01); *A61F 2310/00155* (2013.01); *A61F 2310/00227* (2013.01); *A61F 2310/00239* (2013.01)

(58) Field of Classification Search
CPC ...... A61F 2002/4475; A61F 2002/4495; A61F 2002/30144; A61F 2002/30143; A61F 2002/30769; A61F 2002/30772; A61F 2002/30784; A61F 2002/30785; A61F 2002/3092; A61F 2002/3093
See application file for complete search history.

(56) References Cited

U.S. PATENT DOCUMENTS

| | | | | |
|---|---|---|---|---|
| 5,549,679 | A * | 8/1996 | Kuslich | 623/17.12 |
| 5,607,424 | A * | 3/1997 | Tropiano | 623/17.16 |
| 5,702,449 | A * | 12/1997 | McKay | 623/17.16 |
| 5,910,315 | A * | 6/1999 | Stevenson et al. | 424/422 |
| 6,206,924 | B1 * | 3/2001 | Timm | 623/17.16 |
| 6,869,445 | B1 * | 3/2005 | Johnson | 623/17.11 |
| 8,287,597 | B1 * | 10/2012 | Pimenta | A61F 2/4611 |
| | | | | 623/17.16 |
| 8,932,356 | B2 | 1/2015 | Kraus | |
| 2003/0100950 | A1 * | 5/2003 | Moret | A61F 2/4465 |
| | | | | 623/17.16 |
| 2004/0122518 | A1 * | 6/2004 | Rhoda | 623/17.11 |
| 2004/0258732 | A1 | 12/2004 | Shikinami | |
| 2005/0021151 | A1 | 1/2005 | Landis | |
| 2005/0085914 | A1 * | 4/2005 | Lange | A61F 2/4465 |
| | | | | 623/17.11 |
| 2005/0107879 | A1 * | 5/2005 | Christensen | A61L 27/306 |
| | | | | 623/17.11 |
| 2006/0241760 | A1 * | 10/2006 | Randall et al. | 623/17.11 |
| 2007/0179610 | A1 * | 8/2007 | Biedermann | A61F 2/44 |
| | | | | 623/16.11 |
| 2007/0203584 | A1 * | 8/2007 | Bandyopadhyay | A61F 2/28 |
| | | | | 623/23.5 |
| 2008/0172095 | A1 * | 7/2008 | Salerni et al. | 606/280 |
| 2010/0228296 | A1 * | 9/2010 | Vraney | A61F 2/447 |
| | | | | 623/17.16 |
| 2011/0082551 | A1 * | 4/2011 | Kraus | 623/17.11 |
| 2011/0224796 | A1 | 9/2011 | Weiland et al. | |
| 2012/0191188 | A1 * | 7/2012 | Huang | A61F 2/447 |
| | | | | 623/17.11 |

FOREIGN PATENT DOCUMENTS

| | | | |
|---|---|---|---|
| FR | 2887760 | A1 | 1/2007 |
| FR | 2889442 | A1 | 2/2007 |
| FR | 2955025 | A1 | 7/2011 |
| WO | 2003000480 | | 1/2003 |
| WO | WO 03000480 | A1 | 1/2003 |
| WO | 2007017612 | | 2/2007 |
| WO | 2008040409 | | 4/2008 |

OTHER PUBLICATIONS

Bartolo, P.J. and J. Gaspar, "Metal filled resin for sterrolithography metal part," CIRP Annals—Manufacturing Technology, 57 (2008) 235-238.*
Materialise, "Metal 3D printing" (http://www.materialise.com/en/manufacturing/3d-printing-technology/metal-3d-printing), downloaded Nov. 3, 2017.*
International Search Report for PCT/EP2011/003715 dated Nov. 15, 2011.
Written Opinion for PCT/EP2011/003715 dated Nov. 15, 2011.
"Osteotomy," Dorland's Illustrated Medical Dictionary, 29$^{th}$ Edition, 2000, p. 1290.

* cited by examiner

SURGICAL IMPLANT

The present invention is directed to a surgical implant for the fusion of two adjacent vertebrae with an upper plane for contacting an upper vertebral body and a lower plane for contacting a lower vertebral body and a tubular structure, wherein the tubular structure is formed by a plurality of tubes running from the upper plane to the lower plane and in substantially horizontal direction throughout one side of the surgical implant straight to the opposite side of the surgical implant. This tubular structure has the advantage that the formation and ingrowth of new bone is promoted and advantaged and that the degree of formation and ingrowth of new bone is detectable by X-ray measurements.

In the prior art solid and hollow implants are known in the area of the spine. They either prevent the ingrowth of bone cells due to their solid structure, or because bone cells display a poor adhesion to their surface, or have a cavity which is too large to be completely filled with endogenous bone cells within a reasonable time and therefore are usually filled artificially with a bone substitute material or bone chips. Thus the through growth of newly formed bone is achieved in moderate time while the outer surface is overgrown at a rather sluggish rate.

Such intervertebral implants are generally denominated as cages. Metal cages have the advantage over polymeric cages that bone cells have a better adhesion to the metal surface. Thus the metal cages get grown through in a shorter time in comparison to plastic cages or cages made of polymeric material. However metal cages are radiopaque and thus have the disadvantage that the degree of the formation of new bone and the degree of ingrowth and through growth of new bone cannot be detected by X-ray spectroscopy and thus cannot be detected at all, since other methods than radiography are not available.

The aim of a fusion of vertebrae is bone formation, for instance by cages in the spine area, to achieve long-term stability. The growth of bone cells into and finally through the implant and around the implant is desirable insofar that bone cells can renew themselves, like elsewhere in the body and thus guarantee long-term stability, because body's own bones are in a continuous process of degradation and formation. The cages thus serve as a temporary placeholder so that the intervertebral disc space does not diminish, and thus loses height. Therefore, the cages primarily have to take over static functions, at least until the formation of bones through the implant has taken place. A quick and stable growth of bone cells through an artificial intervertebral implant, such as a cage, is most desired, because such implants come closest to the natural intervertebral disc and represent the most advantageous embodiment for the patient.

The disadvantage of a solid implant such as a solid cage is obvious: A growth of bone cells through the implant is not possible, i.e. the implant must permanently assume the supportive function and thus is less effective in the long run. If an implant is used as a mere spacer there is further the risk that the implant sinks into the vertebrae and the desired distance is no longer guaranteed. Such drawbacks could be avoided for example if the bones grow through the implant naturally.

Hollow implants, such as hollow cages are used with or without bone replacement material. These implants, however, have the disadvantage that the bone cells would have to fill a large cavity, if no bone replacement material is used to fill the implants and therefore the implant would have to assume the supportive function for too long with the above-described disadvantages. If bone replacement materials are used they serve to stimulate the growth of bone cells. Since blood is the catalyst for bone formation but the inner cavity of the cage is filled with bone replacement material and therefore is not sufficiently supplied with blood, a natural growth of bones through the cage partly filled with bone replacement material is insufficient. This in turn means that a growth of bones through a cage partly filled with bone replacement material doesn't take place either in the desired manner.

Therefore it would be ideal to have a bioresorbable artificial intervertebral disc, which takes over the support function until the endogenous bones have replaced it and can take over the support functions by their own. Such embodiments have not been realized yet due to a lack of suitable materials. One reason for this is the fact that no biodegradable materials are available which ensure sufficient stability while the bone is building up. The degradation rate can't be regulated either with sufficient accuracy, because bone formation and the resorption of the implant have to occur at exactly the same speed in order to prevent that a fragile transition structure is formed.

Bone-joining or bone-bridging implants would be desirable which on the one hand provide sufficient mechanical stability and on the other hand can be grown through as completely as possible with endogenous bone cells.

Moreover, it is desirable to monitor bone ingrowth by spectroscopic methods such as X-ray spectrometry, radiography or X-ray exposures in order to determine if and to which extent new bone is grown into and through the cage and how good the cage structure and the cage material are accepted by the body and by the bone cells which have to adhere and grow into the cage.

Thus it is the objective of the present invention to provide an implant for fusion of two adjacent vertebrae, wherein the implant should support the formation of new bone, should accelerate the ingrowth and growth through of new bone and should allow detection of the degree of formation of new bone and the degree of growth of new bone into and through the implant.

This disadvantage is overcome by the inventive surgical implant with its particular tubular structure that facilitates blood flow and thus the transport of bone cells into the implant. It supports and accelerates the through growth of the implant and thus the augmentation of new bone tissue inside the cavity and throughout the implant by using capillary forces. Moreover, it is desirable that the bone formation inside the implant can be monitored by means of spectroscopic methods such as X-ray spectrometry or X-ray measurements for verifying that new bone material is built and to which degree, thus providing a measure how well the implant has been accepted by the patient's body. To allow such monitoring is a further advantage of the inventive surgical implant, as will be shown in the following in detail, because the X-ray spectroscopy can be made through the horizontal tubes.

The objective of the present invention is solved by providing an implant according to claim 1. Further advantageous features, aspects and details of the invention result from the dependent claims, the description, examples and figures.

The present invention discloses a surgical implant with an upper plane for contacting an upper vertebral body and a lower plane for contacting a lower vertebral body and a tubular structure, wherein the tubular structure is formed by a plurality of tubes running from the upper plane to the lower plane and in horizontal direction or in substantially horizontal direction throughout one side of the surgical implant straight to the opposite side of the surgical implant.

The present invention also discloses a surgical implant with an upper plane for contacting an upper vertebral body and a lower plane for contacting a lower vertebral body and a tubular structure, wherein the tubular structure is formed by a plurality of tubes running from the upper plane to the lower plane and in horizontal direction or in substantially horizontal direction throughout one lateral side of the surgical implant straight to the opposite lateral side of the surgical implant.

Moreover the present invention discloses a surgical implant with an upper plane for contacting an upper vertebral body and a lower plane for contacting a lower vertebral body and a tubular structure, wherein the tubular structure is formed by a plurality of vertical tubes running from the upper plane to the lower plane and by a plurality of horizontal tubes running in horizontal direction or in substantially horizontal direction throughout one side of the surgical implant straight to the opposite side of the surgical implant.

Furthermore the present invention discloses a surgical implant with an upper plane for contacting an upper vertebral body and a lower plane for contacting a lower vertebral body and a tubular structure, wherein the tubular structure is formed by a plurality of vertical tubes running from the upper plane to the lower plane and by a plurality of horizontal tubes running in horizontal direction or in substantially horizontal direction throughout one lateral side of the surgical implant straight to the opposite lateral side of the surgical implant.

The present invention relates still to a surgical implant with an upper plane for contacting an upper vertebral body and a lower plane for contacting a lower vertebral body and a tubular structure, wherein the tubular structure is formed by a plurality of tubes in vertical direction or in substantially vertical direction throughout the upper plane to the lower plane and in horizontal direction or in substantially horizontal direction throughout one side of the surgical implant straight to the opposite side of the surgical implant.

The present invention relates also to a surgical implant with an upper plane for contacting an upper vertebral body and a lower plane for contacting a lower vertebral body and a tubular structure, wherein the tubular structure is formed by a plurality of tubes in vertical direction or in substantially vertical direction throughout the upper plane to the lower plane and in horizontal direction or in substantially horizontal direction throughout one lateral side of the surgical implant straight to the opposite lateral side of the surgical implant.

The above-mentioned embodiments of the present invention are directed to implants, especially cages for fusing adjacent vertebrae, which do not comprise an inner cavity or an inner volume which is fillable with bone grafts or fine bone chips bone replacement material or bone cement or artificial bone material or this cavity or volume is reduced to a single vertical tube or a group of 2 to 100 vertical tubes.

In case the present invention is directed to embodiments having an inner cavity or an inner volume which could be filled with bone grafts or fine bone chips or bone replacement material or bone cement or artificial bone material and which is not reduced to or represented by a single vertical tube or a group of 2 to 100 vertical tubes, such embodiments are defined as follows.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of tubes running from the upper plane to the lower plane and in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

The boundary layer actually forms the implant, because the boundary layer is the implant with the inventive tubular structure and the inner cavity or volume which is just a hole in the implant which can be filled with bone taken from patient's body or artificial bone material. Thus the upper plane and lower plane of the implant are in case of implants with cavity or volume the upper plane or lower plane of the boundary layer.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of tubes running from the upper plane to the lower plane and in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of tubes running from the upper plane to the lower plane and in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of tubes running from the upper plane to the lower plane and in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of vertical tubes running from the upper plane to the lower plane and by a plurality of horizontal tubes running in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of vertical tubes running from the upper plane to the lower plane and by a plurality of horizontal tubes running in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of vertical tubes running from the upper plane to the lower plane and by a plurality of horizontal tubes running in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of vertical tubes running from the upper plane to the lower plane and by a plurality of horizontal tubes running in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of tubes in vertical direction or in substantially vertical direction throughout the upper plane to the lower plane and in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of tubes in vertical direction or in substantially vertical direction throughout the upper plane to the lower plane and in horizontal direction or in substantially horizontal direction throughout one side of the surgical implant straight to the opposite side of the surgical implant. The at least one cavity is fillable with bone grafts or fine bone chips or bone replacement material or bone cement or artificial bone material.

Disclosed is a surgical implant with an upper plane for contacting an upper vertebral body and a lower plane for contacting a lower vertebral body, at least one cavity in the center of the implant and a boundary layer around the cavity with a tubular structure, wherein the tubular structure is formed by a plurality of tubes in vertical direction or in substantially vertical direction throughout the upper plane to the lower plane and in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

The present invention also discloses an implant with an upper plane for contacting an upper vertebral body and a lower plane for contacting a lower vertebral body, at least one cavity in the center of the implant and a boundary layer around the cavity between the upper plane and the lower plane with a tubular structure, wherein the tubular structure is formed by a plurality of tubes in vertical direction or in substantially vertical direction throughout the upper plane to the lower plane and in horizontal direction or in substantially horizontal direction throughout one lateral side of the surgical implant straight to the opposite lateral side of the surgical implant. The at least one cavity is fillable with bone grafts or fine bone chips or bone replacement material or bone cement or artificial bone material.

The boundary layer has preferably a minimal thickness of 1.5 mm.

Moreover the present invention is related to a surgical implant, wherein the implant has an upper plane for contacting an upper vertebral body and a lower plane for contacting a lower vertebral body, at least one cavity in the center of the implant and a boundary layer around the cavity between the upper plane and the lower plane, this boundary layer having a minimal thickness of 1.5 mm and a tubular structure, wherein the tubular structure is formed by a plurality of tubes in vertical direction or in substantially vertical direction throughout the upper plane to the lower plane and in horizontal direction or in substantially horizontal direction throughout one side of the boundary layer to the opposite side perpendicular to the tubes in vertical direction or in substantially vertical direction. The at least one cavity is fillable with bone grafts or fine bone chips or bone replacement material or bone cement or artificial bone material.

Because of their particular structure the inventive surgical implants are grown through and grown over by bone cells in a better, more stable and also more rapid fashion than those surgical implants known in the art. The cages of the state of the art are grown through in about 6 to 8 months while the inventive implants are grown through in about 3 to 4 months.

Thus they lead to an optimized fusion of the two bridged vertebral bodies. The aim of a vertebrate fusion by means of cages for instance is an optimal growth of bone cells throughout the implant and around the implant because long-term stability can be achieved best this way. When the bone grows through and around the implant it bears the advantage that bone cells can renew themselves as anywhere else in the organism. This ensures the longevity of the fusion of two adjacent vertebral bodies. Thus the cages serve as temporary placeholders and not as permanent placeholders for preventing the vertebral bodies to sink into the intervertebral disc space, thereby reducing this space. For this reason these cages also have to be the primary static elements, at least until the implant is grown through and grown over with the bone cells. A rapid and stable through growth of an artificial intervertebral disk implant such as a cage is a principal aim since this kind of implants resembles most a natural intervertebral, disk and therefore is the most advantageous treatment form for the patient.

Thus the inventive implants with or without inner cavity or inner volume fillable with bone grafts or fine bone chips or bone replacement material or bone cement or artificial bone material support the formation and ingrowth and growth through of new bone into and through the implant, because blood is permanently sucked into the tubular structure thereby bringing bone cells into the tubular structure which adhere to the surfaces of the tubes and start forming new bone in and around the implant. Moreover the horizontal tubes allow the recordation of X-ray measurements through these tubes and thus through the implant so that tubes filled with newly formed bone can be distinguished from empty tubes and empty tubes as well as tubes filled with bone can be distinguished from the cage material. Moreover especially the horizontal tubes ensure that the capillary forces are still there even when the new bone is partly grown in and grown through the tubular structure of the implant and when the new bone has already filled and occluded most of the vertical tubes especially in the vicinity of the vertebrae. Moreover the horizontal tubes promote and support not only the bone cell adhesion and bone formation within the tubular structure and thus within the implant but also the delivery of bone cells to the outer surface of the implant and the adhesion of bone cells to the outer surface of the implant and thus the overgrowth of the outer surface of the implant with new bone so that finally the complete implant is located within newly formed bone bridging the two adjacent vertebrae. Thus the inventive horizontal tubes have three advantages, namely they sustain the capillary forces so that the high velocity with which the implant is grown through with new bone is maintained; second they are able to deliver bone cells to the outer surface of the implant due to the fact that the horizontal tubes run straight through the implant from one side, especially lateral side to the other side, especially lateral side, of the implant so that overgrowth of the implant with new bone is promoted and supported and third the horizontal tubes allow conducting an X-ray spectrum through the horizontal tubes in order to determine the degree and velocity of bone formation within the horizontal tubes and reasoned from that the degree and velocity of new bone formation throughout the complete implant.

The tubular structure inside the cage or the artificial surgical implant serves for a specific augmentation of the blood flow through the implant by using capillary forces. It thus enables bone growth throughout the entire boundary layer or if no inner cavity is present throughout the entire implant. After some time the boundary layer o the implant is completely grown through. The outer shape of the inventive surgical implant may resemble that of such implants known in the art. The inventive aspect is the tubular structure running through the boundary layer if an inner cavity is present or through the entire implant if no inner cavity is present and not the outline or shape of the implant. It has to be mentioned again that the inventive cages may have an inner cavity which can be filled with bone grafts or fine bone chips or bone replacement material or bone cement or artificial bone material or may not have an inner cavity. However also the inventive implants without inner cavity can be filled by filling the vertical tubes with bone grafts or fine bone chips or bone replacement material or bone cement or artificial bone material. However if the inventive cages do have an inner cavity or volume, the cage is formed or is represented by the boundary layer. Thus any reference to the boundary layer is a reference to the cage itself. Cages without inner cavity or inner volume are referred to as cages as such, since they have no boundary layer around an inner cavity, because they do not have an inner cavity. Thus cages without inner cavity are called herein "cages" and cages with an inner cavity are called herein "boundary layer". The term "implant" as used herein refers to both, cages without inner cavity and cages with inner cavity, i.e. boundary layers.

The vertical tubes or substantially vertical tubes start at the bone contacting upper plane of the boundary layer or implant. Therefore the openings of the tubes are directed towards the bone. At the same time they run through the implant to the lower side or also to the boundaries of the inner cavity, depending on the embodiment. Preferably, the vertical tubes or substantially vertical tubes end in the openings of the lower plane facing the adjacent lower vertebral body. Thus it is preferred that the openings of the vertical tubes face the vertebra. The vertical tubes or substantially vertical tubes run preferably straight from the upper plane of the implant or boundary layer to the lower plane of the implant or boundary layer. But it is also possible that these tubes do not run straight from the upper plane to the lower plane. It is also possible that the vertical tubes or substantially vertical tubes end within the implant and/or run spiral-like, zig-zag-like, snaky, loopy, curved or random-like through the implant. It is only important that the vertical tubes are interconnected to each other so that capillary forces can occur and that the vertical tubes are not dead-end tubes without any opening if the top of the tube is sealed.

The substantially horizontal tubes run from the outer surface of the implant with an inner cavity, respectively from the outer surface of the boundary layer towards the surface facing the inner cavity. Thus these horizontal tubes which run through the inner cavity start at the outer surface of the boundary layer and run straight through the boundary layer to the inner surface of the boundary layer, cross the inner cavity until they reach the opposite inner surface of the boundary layer and again continue to run straight through the opposite boundary layer until they reach the opposite outer surface of the opposite boundary layer. Because of this structure it is possible that the implant is provided with blood from each direction. This is the reason why the through growth of the implant itself as well as of the cavity can be achieved in a shorter time. Moreover since these horizontal tubes run straight through the entire implant, X-ray measurements can be conducted through these tubes and thus through the entire implant in order to detect degree and velocity or defects of ingrowth and through-growth of new bone.

In case the implant does not have an inner cavity, the horizontal tubes run straight through the cage from one side, especially lateral side, to the other side, especially lateral side and allow also the pass through of X-ray beams.

Contacting face refers to a surface of the implant that comes into contact with the adjacent vertebral body, either on the upper plane with the upper vertebral body or on the lower plane with the corresponding lower vertebral body. In the embodiment in which the boundary layer encircles the inner cavity the contacting face depends directly on the thickness of the boundary layer. Preferentially, the upper plane of the boundary layer corresponds to the contacting face towards the upper vertebral body and the lower plane of the boundary layer corresponds to the contacting face towards the lower vertebral body.

According to the invention the vertical tubes run preferably in a substantially parallel manner and are also preferably straight, i.e. the vertical tubes preferably don't show any bends, curves, arcs or the like but run from their start to their end in a substantially parallel manner. In this way they run through the entire boundary layer. Therefore the vertical tubes preferably don't change their radius or diameter continuously or abruptly on their way through the implant, regardless whether the tubes have a round, oval and/or polygonal shape. However this is due to the manufacturing process the preferred design of the vertical tubes but the design of the vertical tubes is not essential to the invention as long as the capillary forces arise and the vertical tubes are not dead-end tubes. Concerning the shape of any tube the angled shapes are preferred over the round, oval or curved shapes, because quicker through-growth of new bone was observed by such angled tubes.

The term "in a substantially parallel manner" shall be understood this way that certain tolerance margins may occur which, however, don't influence significantly the generally parallel pattern of the tubes. The tubes don't vary in their diameter on their way through the implant, notwithstanding a manufacturing tolerance.

The term "straight" as used herein shall describe that the tubes don't show any curves, kinks, bends or the like. Ideally, one may look through each of the tubes, either from the upper plane to the lower plane, from one side of the implant to the opposite side, or from one outer surface to the inner cavity, depending on the embodiment. Thus a light beam may run through the implant along a straight line.

The substantially vertical or substantially horizontal tubes may have any shape. They may exhibit the form of holes or cuts, round, circular, point-shaped, punctiform, cylindrical, oval, square, wedge-shaped, triangular, quadrangular, pentagonal, hexagonal, heptagonal, octagonal or any other configuration. Preferred, however, are embodiments with interior angles larger than 90°, i.e. starting from a pentagon over a polygon to a circle or an oval, while angled form from pentagon to decagon are more preferred. Further preferred are pentagonal, hexagonal, heptagonal and octagonal embodiments and in particular hexagonal tubes and combinations of hexagonal and pentagonal tubes such as in a soccer ball. Edged tubes such as quadrangular, pentagonal, hexagonal, heptagonal, octagonal or polygonal with up to 12 sides are preferred over round or oval tubes without edges, as the bone cells adhere better to the angles, thereby promoting and accelerating bone growth and the through growth of the implant.

Dimensions of the Implant and Tubular Structure:

The implant is to be implanted in such a way that the upper plane and the lower plane of the boundary layer is oriented towards the upper and the lower vertebral body, respectively. For those embodiments wherein the inner cavity is open towards the upper plane and the lower plane it can be described in an analogous manner, the upper plane and the lower plane of the inner cavity face the respective adjacent vertebral body. In this case the openings of the inner cavity are parallel to the longitudinal axis of the spine. Only the upper plane and the lower plane of the boundary layer get in contact with the adjacent vertebral bodies in these embodiments. If the implant does not have an inner cavity, the upper plane is the upper surface of the cage and the lower plane is the lower surface of the cage.

In the embodiments with inner cavity the boundary layer has a minimal thickness of 1.5 mm, measured at the upper and the lower side at the thinnest site of the boundary layer. This means that the boundary layer must have at its upper plane and its lower plane a minimal thickness of 1.5 mm. Preferentially, the boundary layer has a thickness of 1.5 mm to 15.0 mm, more preferred of 2.0 mm to 10.0 mm, further preferred of 2.5 mm to 8.0 mm, still further preferred of 3.0 to 7.0 mm, still further preferred of 3.5 to 6.5 mm, and most preferred of 4.0 mm to 6.0 mm.

Particularly preferred, the thickness of the material corresponds to the half of the height of the implant. The ratio of the height of the implant and the thickness of the boundary layer could be also 15:1 in an extreme case. Further, it is preferred that the lateral parts or sections of the boundary layer don't change their thickness between the upper plane and the lower plane.

In round tubes the cross-sectional area equals the circular area and can be easily determined with $\pi r^2$ wherein r is the tube radius.

Preferentially, at least 55%, more preferred at least 65% and particularly preferred at least 75% of all vertical tubes have a cross-sectional area in the range of 7,800 $\mu m^2$ to 7,500,000 $\mu m^2$, more preferred of 50,000 $\mu m^2$ to 3,100,000 $\mu m^2$, further preferred of 100,000 $\mu m^2$ to 800.000 $\mu m^2$, still further preferred of 125,000 $\mu m^2$ to 650,000 $\mu m^2$ and particularly preferred of 160,000 $\mu m^2$ to 570,000 $\mu m^2$.

The vertical tubes run preferably from the upper plane of the boundary layer to its lower plane wherein the vertical tubes running in the proximity of the exterior surface or the interior surface may have only a partial structure of the vertical tubes. Especially in FIG. 7 it can be seen that most vertical tubes are hexagonal, but in the periphery of the boundary layer there are trimmed hexagonal shapes, i.e. tubes with four sides, three lateral sides according to the lateral sides of the hexagon and a side along the central diagonal of the hexagon. Also in FIG. 9 it is shown that the vertical tubes in the periphery of the implant are cut off and do not show the regular hexagonal structure.

According to the invention also the horizontal tubes run preferably substantially in parallel and straight, i.e. the horizontal tubes don't have a bend, curve, kink, arc or the like but run substantially in parallel from the outer surface towards the inner surface of the boundary layer, or throughout the entire boundary layer. Moreover, the horizontal tubes don't change their radius or diameter abruptly or in a staggered manner during their course, not regarding whether they are round, oval or polygonal.

Further, it is preferred that the horizontal tubes running through the inner cavity are straight and parallel from one exterior side of the implant to the opposite side. This means that these horizontal tubes that end in the inner cavity can be thought as continued on the opposite side of the inner cavity. In other words, a straight line or a light beam can be fancied through such a horizontal tube that runs from one exterior side to the inner cavity and from the opposite side of the inner cavity in an analogous horizontal tube to the opposite exterior side of the boundary layer.

Preferentially, at least 75%, more preferred at least 85% and particularly preferred at least 95% of all horizontal tubes have a cross-sectional area in the range of 7,800 $\mu m^2$ to 7,500,000 $\mu m^2$, preferably 8,000 $\mu m^2$ to 7,000,000 $\mu m^2$, more preferred of 50,000 $\mu m^2$ to 3,100,000 $\mu m^2$, further preferred of 100,000 $\mu m^2$ to 800.000 $\mu m^2$, still further preferred of 125,000 $\mu m^2$ to 650,000 $\mu m^2$ and particularly preferred of 160,000 $\mu m^2$ to 570,000 $\mu m^2$.

The expression that 85% of all tubes have a cross-sectional area inside the aforementioned ranges means that 85 out of 100 tubes have a cross-sectional area inside this range and the remaining 15% may have a smaller or a larger, even an extremely smaller or an extremely larger cross-sectional area. Normally 65% to 90% and preferably 70% to 85% of all vertical tubes have a comparable regular size and are not cut off at the periphery of the implant. Thus at least 60% of all vertical tubes, preferably at least 65%, more preferably 70%, still more preferably 75% and most preferably 80% of all vertical tubes are not cut off and have a comparable size, the same diameter, the same shape and the same cross-sectional area and have a regular shape. The term "the same" refer to variations of up to 10%.

It is further preferred that the upper plane of the boundary layer or of the cage has per $cm^2$ surface at least 10 tubes, more preferred at least 15 tubes, further preferred at least 20 tubes, further preferred at least 30 tubes, further preferred at least 40 tubes, further preferred at least 50 tubes, further preferred at least 60 tubes, further preferred at least 70 tubes, further preferred at least 80 tubes, further preferred at least 90 tubes, further preferred at least 100 tubes, further preferred at least 110 tubes, further preferred at least 120 tubes, further preferred at least 130 tubes, further preferred at least 140 tubes, and particularly preferred at least 150 tubes. It is further preferred that the lower plane of the boundary layer or the cage has per $cm^2$ surface at least 10 tubes, more preferred at least 15 tubes, further preferred at least 20 tubes, further preferred at least 30 tubes, further preferred at least 40 tubes, further preferred at least 50 tubes, further preferred at least 60 tubes, further preferred at least 70 tubes, further preferred at least 80 tubes, further preferred at least 90 tubes, further preferred at least 100 tubes, further preferred at least 110 tubes, further preferred at least 120 tubes, further preferred at least 130 tubes, further preferred at least 140 tubes, and particularly preferred at least 150 tubes. Further it is preferred that the exterior surface of the boundary layer or the cage has per $cm^2$ surface at least 2 tubes, more preferred at least 5 tubes, more preferred at least 10 tubes, more preferred at least 15 tubes, more preferred at least 20 tubes, more preferred at least 25 tubes, more preferred at least 30 tubes, more preferred at least 35 tubes, and particularly preferred at least 40 tubes.

In regard of the round or approximately round tube shapes it is preferred when all vertical tubes or at least 75% of them, preferred at least 85% of them, more preferred at least 90% of them and particularly preferred at least 95% of them have a diameter of 100-3000 μm, more preferred of 250-2000 μm, further preferred of 350-1000 μm, still further preferred of 400-900 μm and particularly preferred of 450-850 μm.

With polygonal tube shapes the diameter is the distance of two opposite parallel sides in even-numbered polygons (quadratic, hexagonal, octagonal etc.), or the distance of a corner to the center of the opposite side in odd-numbered polygons (triangular, pentagonal, heptagonal etc.).

In regard of the pentagonal, hexagonal, heptagonal, octagonal and especially hexagonal tube shapes it is preferred when all vertical tubes or at least 75% of them, preferred at least 85%, more preferred at least 90% of them and particularly preferred at least 95% of them have a diameter of 100-3000 μm, more preferred of 500-2000 μm, further preferred of 700-1500 μm, still further preferred of 800-1300 μm and particularly preferred of 900-1100 μm.

The horizontal tubes through which the radiograph or X-ray spectrum should be measured should preferably have a diameter >500 μm, more preferably >750 μm and most preferably >900 μm. Moreover these sort of horizontal tubes should be parallel to each other. In addition such sort of horizontal tubes should preferably be equally distributed and should preferably run from one lateral side of the implant straight to the other lateral side. Moreover it is preferred at this sort of horizontal tubes comprises the so-called 7" tubes which do not cross the inner cavity and do not have a direct opening to the inner cavity.

In regard of the round or approximately round tube shapes it is preferred when all horizontal tubes or at least 75% of them, preferred at least 85% of them, more preferred at least 90% of them and particularly preferred at least 95% of them have a diameter of 200-4000 μm, more preferred of 300-3000 μm, further preferred of 400-2500 μm, still further preferred of 500-2000 μm and particularly preferred of 600-1500 μm. With polygonal tube shapes the diameter is the distance of two opposite parallel sides in even-numbered polygons (quadratic, hexagonal, octagonal etc.), or the distance of a corner to the center of the opposite side in odd-numbered polygons (triangular, pentagonal, heptagonal etc.). In regard of the pentagonal, hexagonal, heptagonal, octagonal and especially hexagonal tube shapes it is preferred when all horizontal tubes or at least 75% of them, preferred at least 85%, more preferred at least 90% of them and particularly preferred at least 95% of them have a diameter of 100-3000 μm, more preferred of 500-2000 μm, further preferred of 700-1500 μm, still further preferred of 800-1300 μm and particularly preferred of 900-1100 μm.

The wall thickness of the vertical as well as of the horizontal tubes is 50 to 800 μm, preferred 80 μm to 700 μm and further preferred 100 μm to 600 μm, still further preferred 150 μm to 500 μm, still further preferred 200 μm to 400 μm. Preferentially, the diameter of the vertical as well as of the horizontal tubes amounts to the two-fold up to the six-fold of the wall thickness.

The vertical tubes run preferably in parallel, or at least in parallel in certain groups of vertical tubes. It isn't absolutely necessary that all vertical tubes run in parallel. This means that the vertical tubes can be divided into two, three, four, five, six, seven, eight, nine, ten or more groups and that inside such a group all vertical tubes run substantially in parallel. It is further preferred that the vertical tubes or at least those from one group run in parallel to the longitudinal axis of the spine. Preferentially, there are not more than 20 groups, more preferred not more than 10 groups and particularly preferred not more than 5 groups of vertical tubes.

The same applies for the horizontal tubes, as there can be two, three, four, five, six, seven, eight, nine, ten or more groups of them. Preferentially, there are not more than 20 groups, more preferred not more than 10 groups and particularly preferred not more than 5 groups of vertical tubes. It is further preferred that the horizontal tubes or at least those from one group run in perpendicular to the longitudinal axis of the spine. In a preferred embodiment, there are two species of horizontal tubes, wherein one species extends from the lateral side of the implant to the opposite side and the second species extends in a perpendicular or approximately perpendicular manner or in an angle between 60° and 120° in regard of the first species from the posterior to the anterior side. These groups or species of horizontal tubes can be locally separated or also alternating. Thus each of these groups or species can be arranged in a limited section of the boundary layer, or the horizontal tubes of one of these species can be distributed all over the boundary layer. Thus all tubes that run in parallel belong to one of these groups, not regarding if they all are concentrated in a relative proximity or they are dispersed over the entire boundary layer.

Preferentially, the horizontal tubes run in perpendicular, i.e. at right angles to the vertical tubes. It is further preferred that the angle between the vertical and the horizontal tubes is between 45° and 135°, more preferred between 65° and 115°, further preferred between 75° and 105° and still further preferred between 85° and 95°.

In the implants without inner cavity, at least one group of horizontal tubes runs straight through the implant from one side, especially lateral side, to the other side, especially lateral side so that an X-ray spectrum or a radiography measurement can be taken through these horizontal tubes.

In the implants with inner cavity, at least one group of horizontal tubes runs straight through the implant from one side, especially lateral side, to the other side, especially lateral side without crossing the inner cavity so that an X-ray spectrum or a radiography measurement can be taken through these horizontal tubes. These horizontal tubes are referred herein as horizontal tubes 7". Moreover it is preferred that at least one group of the other horizontal tubes (7') run straight through the boundary layer, pass the inner cavity and continue to run straight through the opposite boundary layer so that also X-ray beams can pass through these horizontal tubes (7') as long as the inner cavity is not filled with bone grafts or fine bone chips or bone replacement material or bone cement or artificial bone material.

The inventive implants have a porosity of the entire implant of at least 70%, preferably of at least 75%, more preferably of at least 80% and most preferably of at least 85%. A porosity of 85% means that the entire volume of the implant consists of 85% hollow space (namely the tubes and openings) and of 15% solid material.

Moreover the tubular structure has a porosity of at least 75%, preferably of at least 79%, more preferably of at least 83% and most preferably of at least 87%.

In addition in order to support adhesion of bone cells the inventive implants have preferably a roughness of all surfaces, including the surfaces of the tubes of 6.0 Ra to 8.5 Ra, preferably of 6.2 Ra to 8.0 Ra, more preferably of 6.3 Ra to 7.5 Ra, still more preferably of 6.4 Ra to 7.0 Ra and most preferably of 6.5 Ra to 6.8 Ra.

Moreover the inventive implant provides a total surface area for bone cell adhesion of at least 1.500 mm$^2$, and normally a rang of 1.900 mm$^2$ to 4500 mm$^2$ depending on the size of the implant. The total surface area is defined as the sum of all surfaces of the implant to which bone cells can adhere which are the inner surfaces of the tubes, the surface of the inner wall of the boundary layer surrounding the inner cavity (if present), the surfaces of any opening within the tubes and any cuts through the tubes and the surface of the outer surface of the cage. In regard to the volume of the cage material which is only the volume of the solid part of the cage without the volume of the tubes, the inventive implants have an extremely high ratio of volume of the material to total surface area. Thus preferably the ratio of volume of cage material to total surface area is between 180 µm and 250 µm, preferably between 190 µm and 240 µm, more preferably between 200 µm and 230 µm and most preferably between 205 µm and 225 µm. Thus, if a cage has a volume of the cage material such as titanium of 708 mm$^3$ and a total surface area of 3198 mm$^2$, the ration of volume of cage material to total surface area is 708 mm$^3$/3198 mm$^2$=0.221 mm=221 µm.

Thus the inventive implants are characterized by the tubular structure which consists of a plurality of horizontal tubes and a plurality of vertical tubes which provide an extremely high total surface area for the adhesion of bone cells and which make use of capillary forces in order to suck blood into the tubular structure which is the carrier for the blood cells. Moreover the horizontal tubes or at least some horizontal tubes run straight through the implant and can be used to conduct X-ray spectra or radiographs through these tubes in order to detect the degree, area, completeness and velocity of through growth of new bone through the implant or the conversion of bone replacement material or artificial bone material or autologous bone chips or autologous bone grafts or cancellous bone mass into new bone. In case an implant with inner cavity is filled with bone cement or cortical bone mass which is not distinguishable from newly formed bone, the horizontal tubes (herein called tubes 7") which run straight through the implant and do not cross the inner cavity can be used for conducting X-ray spectra or radiographs in order to assess degree, area, completeness and velocity of through growth of new bone through the implant or the conversion of cortical bone mass into new bone. Still moreover the tubular structure can perform micro-movements, since the vertical tubes have a flexibility due to the presence of the horizontal tubes which allows such micro-movements although the vertical tubes do not comprise longitudinal cuts through and along the vertical tubes. These micro-movements stimulate the formation of new bone so that the inventive implants are grown through with newly formed bone much quicker than any implant of the state of the art thereby allowing the newly formed bone to take over the stability function. This is important because the more a cages ensures to be a stable distance keeper the less the bone is forces to take over this function and the less stimulation for the bridged vertebrae is given to form new bone which stably bridges these two vertebrae.

It is evident from the disclosure herein as well as the figures and examples that the inventive implants do not completely or exclusively consist of the tubular structure. The tubular structure is inside the cage if no inner cavity is present or inside the boundary layer if an inner cavity is present. However the tubular structure consisting of the vertical tubes and the horizontal tubes and optionally any additional openings between the tubes has not sufficient stability in order to keep the desired distance or space between the two bridged vertebrae. In order to avoid that the adjacent and bridged vertebrae sink into the cage, the inventive cages have a solid front part without tubes which also comprises a recess for inserting an implantation tool and preferably a solid back part or solid back plane without tubes. Moreover the cages have lateral parts such as a lateral frame which provides a higher stability than the tubular structure within the cage. Of course the horizontal tubes run through these lateral sides but no vertical tubes run through these lateral sides which guarantees the higher stability.

Thus the inventive cages comprise a frame which surrounds the tubular structure within the cage and which ensures that the cage is not deformed by the pressure of the spinal column. The same is true for the implants with an inner cavity where an outer frame is part of the boundary layer and preferably also an inner frame surrounds the inner cavity which is also part of the boundary layer. This frame, outer frame and inner frame has a thickness of preferably 0.2 mm to 7 mm and more preferably of 1 mm to 4 mm. However such frames are not essential to achieve the advantages of the present invention. Such frames ensure sufficient stability of the complete implant and it is known to a skilled person how to design such a frame in order to provide an implant which sufficiently resists the pressures of the spinal column. Almost all cages with inner cavities have such frames or other structures which provide sufficient stability like solid areas, rings or margin areas which do not have any tubes or which only have horizontal tubes. FIG. 10 obviously shows such frames. Shown is one outer frame surrounding the implant. This frame has a thickness of 3 mm. This frames becomes broader at the back part of the implant where the frame has a thickness of 5 mm to 6 mm. The inner cavity is also surrounded by an inner frame having a thickness of 1.2 mm and divided into three parts by two inner walls having a thickness of 0.9 mm.

In a further preferred embodiment of the present invention the inner cavity (2) has one or more and preferentially one, two, three, four or five partitions as shown for instance in FIGS. 9 and 10. They don't interfere with the filling of the inner cavity (2) but offer additional surfaces for the adhesion of new bone cells. In FIGS. 9 and 10 such a further preferred embodiment is shown. Herein, the inner cavity (2) is divided by two partitions.

Most spine surgeons prefer to fill these surgical implants with autologous bone material. For this purpose, bone material is removed from the patient's hip and then used for the filling of the surgical implant. This method is advantageous for the filling of the implant but often causes complications in the hip area from which the bone material was removed. Such complications are well described in literature and can be found under the tag co-morbidity. The inventive surgical implant offers a beneficial solution also for this problem by reducing the volume of the inner cavity and increasing the volume of the implant itself.

The term "volume of the inner cavity (2)" refers to the volume inside the interior surface(s) (9) of the boundary layer (1), thus the volume to be filled with autologous bone material (cortical bone and/or cancellous bone).

"Body volume of the surgical implant" refers to the volume resulting from the outlines of the boundary layer (1), i.e. the mass of the boundary layer (1) and its height to which the volume of the tubes running through the boundary layer has to be added to the body volume. This means the "body volume of the surgical implant" is the volume of the material of the boundary layer (1), respectively the implant, plus the volume occupied by the tubes running through the boundary layer (1). The "body volume of the surgical implant" is thus the volume between the inner surface(s) (9) and the outer surface(s) (8) of the boundary layer (1) and the upper plane (3A) and the lower plane (3B) of the boundary layer (1).

According to the invention the ratio between the volume of the inner cavity (2) and the body volume of the surgical implant ranges between 1:2 (i.e. 50%) and 1:1 (i.e. 100%). In corresponding surgical implants known in the art this ratio is over 130% and in general over 150%. If the inventive embodiment with a partition of the inner cavity is used (as can be seen in FIGS. 9 and 10) the volume of the partition(s) has to be subtracted from the volume of the inner cavity (2) and has to be added to the body volume of the surgical implant.

Furthermore, according to the invention the ratio between the volume of the material of the surgical implant and the volume of the tubes throughout the boundary layer (1) of the surgical implant or throughout the entire cage ranges from 10 vol. %:90 vol. % or from 20 vol. %:80 vol. % (i.e. 20% cage material to 80 vol. % air volume occupied by the tubes) up to 60 vol. %:40 vol. % (i.e. 60% cage material to 40 vol. % air volume occupied by the tubes) and preferentially up to 50 vol. %:50 vol. % and more preferentially 40 vol. % to 60 vol. % and most preferably between 10 vol. %:90 vol. % and 20 vol. %:80 vol. %. In other words, said ratio of cage material to air volume generated by the tubes is thus 1:9 or 2:8 to 6:4, preferentially 5:5 and more preferred 4:6 and most preferred between 2:8 and 1:9. This value is also called porosity. The inventive tubular structure reaches a porosity of 78% to 94%, preferably of 80% to 93%, more preferably of 82% to 92%, still more preferably of 84% to 91% and most preferably of 85% to 90%. That means within the tubular structure most preferably 10% to 15% of the volume are made of the solid cage material such as the metal and 90% to 85% of the volume are hollow space.

The "volume of the material of the surgical implant" corresponds to the "body volume of the surgical implant" minus the "tube volume". The "tube volume" can be determined by measuring the fluid volume needed to fill all tubes with this test fluid. The "tube volume" refers to the volume the vertical and the horizontal tubes occupy together, thus the volume resulting when all tubes in the boundary layer (1) or in the cage are filled. The tube volume as well as the volume of the inner cavity are available for the new bone to be built for growing through the implant. The inventive surgical implant increases significantly the surface for the adhesion of bone cells in comparison with conventional cages. At the same time the material requirement for the production of the inventive implant is reduced without incurring a loss in the stability of the implant. State of the art cages with inner cavity or inner volume provide between 0.1% to 10% of the surface which is provided by the inventive implants for the adhesion of bone cells. State of the art cages with regular or irregular or random-like inner structure provide between 10% and 50% of the surface which is provided by the inventive implants for the adhesion of bone cells, but such state of the art cages have a much lower porosity of 20% to 60%, i.e. 20% to 60% are hollow space while 80% to 60% are cage material. Thus only the inventive implants provide a huge surface area for the adhesion of bone cells in combination with a very high porosity by a structure which is stable, wherein capillary forces occur and through which X-ray spectra can be made.

The inventive surgical implants can stand the same load as a conventional massive cage, i.e. a cage with a massive boundary layer without a tubular structure. However, they have the advantage that the surface for bone cell adhesion from the blood is maximized and the filling volume is significantly reduced. Therefore less autologous bone material has to be removed elsewhere and the co-morbidity can be significantly lowered. The removal of bone material from the hip may even be dropped. The inventive structure of the surgical implant is particularly advantageous when using bioresorbable cage materials, as there is significantly less material that needs to be resorbed by the organism. Because of the tubular structure a more rapid and more stable through growth of the surgical implant is occurring. Thus the adjacent vertebral bodies are more rapidly fused by the new bone tissue lending it a more stable shape. The support and spacer function of the surgical implant can be taken over more rapidly by the new bone tissue. In respect of this time course also a material can be selected for the implant that is more rapidly resorbed.

Moreover, the vertical tubes (5) can be interconnected by holes, openings, recesses, incisions, cuts or tapered cuts without impairing the use of the capillary forces. These incisions into the tube walls of the vertical channels—such as shown in FIGS. 9 and 10—can be disposed over the entire tube length, i.e. maximally from the upper plane (3A) of the boundary layer (1) or the implant to its lower plane (3B), or they may alternate with non incised sections. The connections between the vertical tubes (5) can be evenly or stochastically distributed. Longitudinal cuts, holes, elongated holes or any other conceivable shape may only occur in such a number and size so that the stability of the surgical implant isn't impaired.

A particularly preferred embodiment of the inventive surgical implant is now described in respect of FIG. 7. This figure shows an inventive surgical implant with its particular tubular structure. The surgical implant is built by the boundary layer (1) surrounding the inner cavity (2). The boundary layer (1) has an upper plane (3A) that is jagged in the present example in order to generate a better anchoring with the adjacent vertebral body, and a likewise jagged lower plane (3B). The boundary layer has a thickness of 4 mm. In ventral direction the surgical implant is tapered in a pointed shape. In dorsal direction the surgical implant has a flattened back side (4). The vertical tubes (5) run from the upper plane (3A) of the boundary layer (1) in a straight and parallel manner to the lower plane (3B) of the boundary layer (1) through the boundary layer (1) to the lower plane (3B) of the boundary layer (1). These vertical tubes (5) have a hexagonal shape and a diameter of 1.0 mm in its full size, i.e. if the vertical hexagonal tubes (5) aren't cut off, as may occur at the edges of the boundary layer (1). 60% to 80% of all vertical tubes have this full size, i.e. they aren't cut off at the edges of the boundary layer and have aforesaid diameter. There are between 50 to 70 vertical tubes per $cm^2$ surface on the upper plane as well as on the lower plane. The wall thickness (6) of these vertical tubes amounts to 0.35 mm. The vertical tubes (5) are interconnected by the horizontal tubes (7). The horizontal tubes (7) run in a straight and parallel manner throughout the boundary layer (1). There are two types of horizontal tubes (7), these tubes (7') running from the outer surface (8) of the boundary layer (1) to the inner surface (9) of the boundary layer (1), and those horizontal tubes (7") not running to and through the inner cavity (2) but only through the boundary layer (1). As horizontal tubes (7') are denominated all horizontal tubes (7) that run from the inner surface (9) of the boundary layer (1) to the outer surface (8) of the boundary layer (1). As horizontal tubes (7") are denominated all horizontal tubes (7) that run from one side of the boundary layer (1) to the opposite side of the boundary layer (1) without crossing the inner cavity (2). The horizontal tubes (7) have a hexagonal shape and a diameter of 1.0 mm in their full size, i.e. when the horizontal hexagonal tubes (7) aren't cut off at the edges of the boundary layer (1). 96% of all horizontal tubes (7) have this full size, i.e. they aren't cut off at the edges of the boundary layer (1) and have this diameter. There are between 40 and 90 horizontal tubes per $cm^2$ outer surface (8) as well as per $cm^2$ inner surface (9). The wall thickness (10) of these horizontal tubes is 0.35 mm.

Examples for such inventive surgical implants are in particular cages for cervical, thoracic or lumbar use (such as ALIF cages, PLIF cages and TLIF cages). The inventive surgical implants are also known as interbody vertebral element, implants for intersomatic fusion or implants for intercorporal vertebral fusion. This fusion can be carried out on natural vertebrae of the patient, artificial (replaced) vertebrae or a natural and an artificial vertebra. Mutatis mutandis this applies also if only parts of a natural vertebra have been replaced.

The contact area with the bone, i.e. the upper plane as well as the lower plane of the boundary layer or the cage, doesn't have to be necessarily even, as in conventional surgical implants of this kind. It may also have an asymmetrical shape. It is also preferred that the vertical tubular structure extends to a small degree over the outer edge of the boundary layer in direction to the respective adjacent vertebral body. The portion of the vertical tubes extending beyond the upper plane or lower plane of the boundary layer may sink or force itself into the adjacent vertebral body, respectively. It thus causes an intended lesion of the surface of these vertebral bodies by which bone growth and blood flow are stimulated in this area which leads to a better through growth of the implant.

Thus the inventive implant may have an even surface towards the adjacent vertebral body on the upper plane as well as on the lower plane. However, it is preferred that this surface may be arched by instance, respectively that the vertical tubes extend beyond the boundary layer and into the upper and/or lower vertebral body. The unevenness of the surface may amount from 0.1 mm to 3 mm, measured from the upper plane or the lower plane of the boundary layer, respectively, to the maximal extension of the vertical tubular structure at the surface. Thus in these embodiments of the inventive implants a portion of the vertical tubes doesn't end at the upper plane and/or lower plane of the boundary layer but extends beyond up to 3 mm maximally.

The arrangement of the tubes and of the tubular structure preferentially has a symmetric pattern. It should be noted that a randomly generated tubular network, as can be found for example in porous structures or sponges isn't suitable to solve the task of the present application because the capillary forces can't be used in a coordinated and reliable manner or are not even present. The same applies for tubes that change their direction and/or their diameter abruptly or are staggered or are generated by a random sequence and/or shape of different layers of a multilayer system for the main body of the implant. Such systems are characterized in that the blood flow is increased only in certain parts of the implants. Consequently, only those delimited parts will be well populated with bone cells. It is also possible that there is only an island population pattern in these implants. In any case there will be no solid and homogenous through growth of the implant, as an entire through growth doesn't occur at all or only at a very slow rate. In the worst case this may even favour malpositions of the patient's spine caused by an uneven integration of the implant which would render surgical interventions indispensable.

It should be kept in mind that the inventive implants provide a high porosity but also a huge surface area which is available for the adhesion and binding of bone cells so that new bone can grow through the implant very soon. In addition the provided tubular structure makes use of capillary forces and also gives the possibility to detect the degree, velocity and location of bone ingrowth and bone through-growth by standard X-ray spectroscopy or radiography.

It is understood that not the entire implant has to display the inventive tubular structure. It is preferred, however, that the vertical tubular structure extends from the upper plane of the boundary layer up to the lower plane of the boundary layer and that the horizontal tubes also extend from the outside of the boundary layer to the inner cavity or to the opposite side of the boundary layer, respectively.

Especially those implants that have continuous and substantially parallel vertical and horizontal tubes showed to be advantageous.

Further, the inventive honeycomb structure of the boundary layer of the inventive surgical implant combines simultaneously the features of good mechanical stability and an optimal filling volume of the inner cavity so that a rapid and stable through growth of the implant with new bone tissue is effectuated while the required bone material is reduced and thereby reducing the co-morbidity.

Bone tissue generally comprises three cell types, osteoblasts, osteocytes and osteoclasts, whereby the developed bone also has a bone top layer of bone lining cells. The presence of blood is essential and needed for optimal bone formation. Ossification (or osteogenesis) is the process of incorporating or sedimenting new bone material by cells called osteoblasts. It is synonymous to bone tissue formation. There are two processes resulting in the formation of normal, healthy bone tissue: Intramembranous ossification is the direct incorporation of bone into the primitive connective tissue (mesenchyme), while endochondral ossification involves cartilage as a precursor. Chondroblasts are the progenitor of chondrocytes (which are mesenchymal stem cells) and can also differentiate into osteoblasts. Endochondral ossification is an essential process during the rudimentary formation of long bones, the growth of the length of long bones, and the natural healing of bone fractures.

In the formation of bones osteoblasts, osteocytes and osteoclasts work together. Osteoblasts are bone-producing cells and responsible for building and therefore preserving the bone. Non-active osteoblasts on the bone surface are called bone lining cells. Osteocytes are former osteoblasts that are incorporated into the bone tissue by ossification. They provide for the preservation of the bone by balancing bone resorption and bone formation. Osteoclasts are responsible for the degradation of the bone. Through them, the thickness of the bone is determined and calcium and phosphate can be released from the bone. The osteoblasts are the cells responsible for bone formation. They develop from undifferentiated mesenchymal cells, or chondroblasts. They attach themselves to bones in the form of dermal layers and indirectly form the basis for new bone substance, the bone matrix, especially by excreting calcium phosphate and calcium carbonate into the interstitial space. In this process they change to a scaffold of osteocytes no longer capable of dividing, which is slowly mineralized and filled with calcium.

The inventive tubular structure facilitates the influx of blood also to the inner cavity by using capillary forces. Therefore also osteoblasts are stimulated to migrate in a short period of time into the tubes and to the filled inner cavity. By this mechanism bone growth is promoted and thus the through growth of the implant with bone tissue is improved and accelerated. This is a clear advantage over similar implants known in the art.

The inventive implant has the advantage over porous structures or sponges that it is hardly deformable, if at all, and is dimensionally stable, has a defined shape and surface and can be handled and implanted by conventional implantation tools without the risk to destroy or to damage the implant or its tubular structure and that X-ray beams can pass through the implant for radiography measurements.

In order to improve the adhesion of bone cells further the inner surfaces of the tubular structure(s) and to the outer surface of the implant and to the inner surface of the inner cavity the surface can be structured or roughened by, for example, any mechanical, chemical or physical roughening. To suppress the growth of bacteria or other germs on the implant surface, it can be provided with antibiotics and the outer surface of the boundary layer or the cage and/or the surfaces of the tubular structure and the inner cavity for example can be provided with a drug eluting coating, in which agents such as antibiotics are stored and can be released continuously.

The inventive implants can be manufactured by standard techniques, for example, using laser technology and laser cutting procedures, rapid prototyping, laser fusion, e.g. Lasercusing® or injection molding and therefore can assume in the context of the described invention any shape.

Preferentially, the inventive implants are manufactured in one piece. They consist completely or at least to 90% of a metal or metal alloy, are not porous as ceramics for instance but have a defined interior tubular structure that stimulates the blood flow through the implant and by this generates optimal conditions for a through growth with new bone tissue. The tubular structure is not only vertical but also allows a blood flow through the horizontal tubes, thus accelerating the through growth and the conversion from an implant to natural bone tissue. This also holds true for inventive implants made of polymers such as carbon fibers, polyether ketones PEEK [poly(ether ether ketone)], PEEEK [poly(ether ether ketone ether ketone)], PEEKEK [poly (ether keton ketone)] or PEKK [poly(ether ether ether ketone)]. The polymeric material is preferably radiolucent. The polymeric material is preferably radiolucent characterized by a Hounsfield unit ≤400.

The inventive surgical implants are preferentially manufactured as one piece or part or monolithic and don't consist of several parts nor are manufactured out of several pieces. The term "one-part surgical implant" or "one-part implant" refers to the implant only and not to any fixation means. For example, such one-part implants can be fixated with screws to the adjacent vertebral body(-ies). Such fixation means are not covered by the term "one-part" and are regarded as accessory to the implant. The same applies for implantation tools. Further, natural materials such as natural bone material or bone cement or bone replacement material for the inventive surgical implant are not part of the implant. Therefore the inventive surgical implants are preferentially one-part, one-piece or monolithic, according to this definition. Embodiments with two parts are still possible, but the maximum is three parts, preferentially there are not more than two parts. In these embodiments the additional parts generally are fixation means such as removable plated for fixation screws or fixation hooks or fixation clamps or fixation claws or the like. In most cases, these additional parts are optional for the inventive implant.

The inventive implants are not assembled according to a modular design or out of several parts or pieces or plates. Empirically, there are often difficulties to connect or to join these different parts without a special effort, or they remain movable one against the other in a translational or rotational or sliding way. The boundary layer building the implant has a defined shape that is not modified after implantation. The inventive surgical implant is not smooth, or plastic or deformable. Neither it is spongy or porous.

In another embodiment of the invention the boundary layer builds the surgical implant itself. These embodiments are directed to implants with an inner cavity or inner volume which can be filled with bone grafts or fine bone chips or bone replacement material or bone cement or artificial bone material. Boundary layer refers herein to the wall around the inner cavity. It can also be defined as a surrounding part. The inventive tubular structure of the boundary layer of this embodiment corresponds to the previously described embodiment. By this structure an inner cavity is formed not in the classical sense that it is surrounded on all sides by the boundary layer. Instead this cavity describes a space left open by the boundary layer that can be described as a continuous opening between the walls of the boundary layer. The boundary layer is closed, so it surrounds this cavity by 360° and builds only the side walls delimiting this cavity. Towards the upper plane and the lower plane this cavity is open. Thus this cavity essentially is a continuous recess extending from the upper plane to the lower plane of the implant. The body of the surgical implant is entirely built by the boundary layer. The boundary layer has an inner surface facing the cavity, an outer surface facing the exterior space and an own upper plane and lower plane shaped by the upper plane and the lower plane of the boundary layer. The interior structure of the boundary layer is built by substantially vertical and substantially horizontal tubes throughout the boundary layer. When contemplated from the outside the implant looks as being provided with "holes", wherein each "hole" represents the ending of such a tube.

In this embodiment the boundary layer doesn't run circularly around the cavity but may have the shape of a heart (see FIG. 6), of a boat (see FIG. 5), or of a rather rectangular body (see FIG. 7). The space delimited by the boundary layer is defined as cavity or inner cavity. This cavity is open to the upper side and to the lower side of the surgical implant.

The present invention relates also to a surgical implant consisting of a metal, a polymeric material or a metal alloy, wherein the implant has an upper plane for contacting an upper vertebral body and a lower plane for contacting a lower vertebral body and a boundary layer around the implant between the upper plane and the lower plane and at least one recess opening to at least one cavity within the implant and a tubular structure extending from the upper plane around the at least one cavity through the lower plane, wherein the tubular structure is formed by a plurality of tubes and the at least one cavity is fillable with bone grafts or fine bone chips or bone replacement material or bone cement or artificial bone material.

The two planes (upper plane and lower plane) are also called horizontal planes. The boundary layer is also referred to as vertical surface. The boundary layer has an outer surface which is the surface around the implant between the upper plane and the lower plane. In the boundary layer there is at least one recess opening of the cavity and preferably the boundary layer has two opposite recess openings of the cavity. The cavity is surrounded by the inner surface of the boundary layer. Tubular structure and the tubes of the tubular structure end on the inner surface of the cavity and do not cross the cavity when filled with bone replacement material or artificial bone material. In case the at least one cavity is filled with bone cement, the implant will comprise a solid core of bone cement and the new bone will grow from the upper vertebral body through the tubes of the tubular structure to the bone cement core and from the lower vertebral body through the tubes of the tubular structure to the bone cement core from the other side. In case the at least one cavity is filled with bone replacement material or especially with artificial bone material, the new bone will grow into the implant from the upper and the lower vertebral body through the tubes of the tubular structure and will convert the artificial bone material to new bone so that new bone will also be formed in the at least one cavity thereby bridging the two adjacent vertebral bodies.

In case the bone replacement material or artificial bone material is liquid or fluid it is preferably used together with a carrier or solid support such as particles or impregnated on a textile-like material.

Moreover it is preferred that the tubes of the tubular structure are parallel to each other or the tubes of the tubular structure are grouped into groups of parallel tubes.

Also preferred is that the tubes of the tubular structure extend along the longitudinal axis of the spinal column.

Furthermore it is preferred that the tubular structure is formed by tubes running along the longitudinal axis of the spinal column and tubes running horizontally or perpendicular to the tubes which run along the longitudinal axis of the spinal column.

Preferably between 60% and 90% of the tubes forming the tubular structure end at the cavity. The implant may comprise one, two, three, four, five or six cavities. Moreover it is preferred that at least one cavity is located in the middle of the implant having one opening in the upper plane or in the lower plane or in the boundary layer or having two openings wherein one is in the upper plane and the other one in the lower plane or both are in the boundary layer.

The present invention relates also to a surgical implant consisting of a polymeric material, wherein the implant has an upper plane for contacting an upper vertebral body and a lower plane for contacting a lower vertebral body and a boundary layer around the implant between the upper plane and the lower plane and at least one recess opening to at least one cavity within the implant and a tubular structure extending from the upper plane around the at least one cavity through the lower plane, wherein the tubular structure is formed by a plurality of tubes and the at least one cavity is fillable with bone replacement material or bone cement or artificial bone material.

Another embodiment of the present invention relates to a surgical implant for replacing an intervertebral disc, wherein the body of the implant consists of a polymeric material and has two planes for contacting the two adjacent vertebral bodies, respectively, a boundary layer and a scaffold zone, wherein the scaffold zone is formed by a plurality of tubular structures and encompasses a cavity fillable with bone replacement material or bone cement. The tubes of the tubular structures preferably extend parallel to one another along the longitudinal axis of the spinal column and the tubes of the tubular structures are preferably interconnected by openings.

The present invention also relates to an intervertebral implant, wherein the body of the implant consists of a polymeric material and has two planes for contacting two adjacent vertebral bodies, a scaffold zone and a boundary layer which partly surrounds the scaffold zone and wherein the scaffold zone encompasses a cavity fillable with bone replacement material or bone cement around which a plurality of vertical tubular structures preferably running along the longitudinal axis of the spinal column and a plurality of horizontal tubes running horizontally from one side to the opposite side of the implant preferably along the transversal axis of the body or preferably in a plane perpendicular to the longitudinal axis of the spinal column.

The present invention also relates to an intervertebral implant, wherein the body of the implant consists of a non-metallic material and has two planes each of them contacting an adjacent vertebral body, a scaffold zone and a boundary layer which partly surrounds the scaffold zone and wherein the scaffold zone is formed by a cavity fillable with bone replacement material or bone cement and a plurality of vertical tubes preferably running along the longitudinal axis of the spinal column and optionally a plurality of horizontal tubes running horizontally from one side to the opposite side of the implant preferably along the transversal axis of the body or preferably in a plane perpendicular to the longitudinal axis of the spinal column. It is preferred that the tubes will end when meeting the cavity filled with the bone replace material. Thus in the preferred embodiments these tubular structures consisting of a plurality of tubes which are preferably parallel to each other do not cross the cavity. These dead-ends of the tubular structures which end in the cavity filled with bone replacement material or bone cement provide a good insertion point or adhesion area for the bone cells because of the comparatively rough surface of the bone replace material. This way these dead-ends become germination centers for the continuous ossification of the tubular structures and thus of the implant.

As used herein the term "tubular structure" refers to the entirety of the tubes while also groups of tubular structures can be present which are formed of certain numbers of tubes. The tubes form the tubular structure or groups of tubes which are preferably parallel to each other within one group form tubular structures which extend around the at least one cavity in the implant.

The present invention relates also to a surgical implant, wherein the body of the implant consists of a polymeric material and has two planes for contacting the adjacent vertebral body respectively, a scaffold zone and a boundary layer which partly surrounds the scaffold zone and wherein the scaffold zone is formed by a cavity fillable with bone replacement material or bone cement and a plurality of vertical tubes running along the longitudinal axis of the spinal column. Preferably also a plurality of horizontal tubes are present running horizontally or perpendicular to the vertical tubes through the implant.

The present invention relates further to an intervertebral implant, wherein the body of the implant consists of a polymeric material and has two planes for contacting two vertebral bodies, a scaffold zone and a boundary layer which partly surrounds the scaffold zone and wherein the scaffold zone is formed by a cavity fillable with bone replacement material and a plurality of vertical tubes running along the longitudinal axis of the spinal column and being parallel to each other. Preferably also a plurality of horizontal tubes are present running horizontally from one side to the opposite side of the implant, with exception of the cavity area.

Furthermore the present invention relates to a surgical implant, wherein the body of the implant consists of a polymeric material and has two planes for contacting two adjacent vertebral bodies, a scaffold zone and a boundary layer which partly surrounds the scaffold zone and wherein the scaffold zone is formed by a cavity fillable with bone replacement material and a tubular structure consisting of a plurality of vertical tubes which extend in preferably straight lines from the top of the upper vertebral body contacting surface to the opposite and being preferably parallel to each other. Preferably a plurality of horizontal tubes are present running horizontally straight through the implant, with exception of the cavity area.

The horizontal tubes preferably connect the vertical tubes with each other. Moreover it is also possible that the horizontal tubes are connected with each other through holes or openings or recesses between adjacent horizontal tubes.

The present invention relates to bone-joining or bone-bridging surgical implants in the form of artificial discs consisting of a polymeric material, wherein the artificial surgical implant exhibits at least one bone-contacting plane and a scaffold zone consisting of a cavity fillable with bone replacement material and a plurality of tubes with defined cross-sectional areas or radii and these tubes of the surgical implant are interconnected so that a three-dimensional network of tubes is formed. Such a three-dimensional network is also referred to as tubular structure.

The present invention further relates to bone-joining or bone-bridging surgical implants in the form of artificial discs consisting of a polymeric material, wherein the artificial disc implant exhibits at least one bone-contacting plane and a scaffold zone consisting of a cavity fillable with bone replacement material or bone cement and a plurality of tubes with defined cross-sectional areas or radii and these tubes of the scaffold zone are interconnected so that a three-dimensional network of tubes is formed, with exception of the cavity area.

It was surprisingly found that bone-joining or bone-bridging surgical implants consisting of a preferably radiolucent polymeric material grow together particularly well with the contacted bone, when the surface of the implant is not smooth or not rough or not porous, but has a scaffold zone, consisting of at least one cavity filled or all filled with bone replacement material or bone cement and a plurality of tubes forming a tubular structure which surrounds the filled at least one cavity. Preferably the tubes are interconnected and form a defined structure, the tubular structure. Concerning the tubular structures it is important that added together at least a total of 20% of all vertical and horizontal tubes run from one side of the implant through the implant to the other side of the implant. The vertical and horizontal tubes running through the implant suck or pull blood by capillary forces into the vertical and horizontal tubes and thereby into the complete tubular structure, which promotes and accelerates new bone formation within the bone-joining or bone-bridging implant.

The present application also relates to a method for treatment of spinal column disorders which comprises the step of implanting a surgical implant as described before into the intervertebral space of a patient in need thereof.

A patient as used herein refers to any mammal including humans suffering from a spinal column disorder. However, it is preferred that the patient is a human.

The term "bone-joining" or "bone-bridging" implies that the implant is in direct contact with a bone. That means at least a part of the plane of the surgical implant touches a bone.

The inventive scaffold zone preferably starts at the bone-contacting plane of the implant, so that the openings of the vertical tubes are facing the bone, i.e. the upper openings are facing the upper contacted vertebral body and the lower openings of the tubes the lower vertebral body. The vertical tubes, the optionally present horizontal tubes, the openings between the tubes as well as the cavity filled with bone replacement material form the scaffold zone.

Each vertical tube is preferably connected by a horizontal tube with at least two openings with the adjacent vertical tubes.

The term "radiolucent polymeric material" refers to anything that permits the penetration and passage of X-rays or other forms of radiation. More specifically, the term "radiolucent polymeric material" as used herein refers to any material that does not impair the ability to distinguish by X-ray exposures between bones and specifically new grown bones and the material of the implant. Such "radiolucent material" can be characterized further by the Hounsfield scale, which is a quantitative scale for describing radiodensity. The Hounsfield unit (HU) scale is a linear transformation of the original linear attenuation coefficient measurement into one in which the radiodensity of distilled water at standard pressure and temperature (STP) is defined as zero Hounsfield units (HU), while the radiodensity of air at STP is defined as −1000 HU. For a material X with linear attenuation coefficient $\mu_x$, the corresponding HU value is therefore given by $$HU = \frac{\mu_X - \mu_{water}}{\mu_{water} - \mu_{air}} \times 1000$$

where $\mu_{water}$ and $\mu_{air}$ are the linear attenuation coefficients of water and air, respectively. Thus, a change of one Hounsfield unit (HU) represents a change of 0.1% of the attenuation coefficient of water since the attenuation coefficient of air is nearly zero. It is the definition for CT scanners that are calibrated with reference to water. Exemplary values are −1000 for air, 0 for water, and >400 for bones.

Thus the intervertebral implant according to the invention is characterized in that the body of the implant consists preferably substantially of a radiolucent polymeric material with a Hounsfield unit ≤400, preferably ≤300, more preferably ≤200, even more preferably ≤100, and most preferably ≤0. Such materials include but are not restricted to fiber-reinforced plastics (glass/carbon fibers with a corresponding matrix), polyether ketones (PEEK—poly ether ether ketone, PEEKEK—poly ether ether ketone ether ketone, PEKK—poly ether keton ketone; PEEEK—poly ether ether ether ketone) or polymer materials in general.

The body of the surgical implant according to the invention substantially consists of one or more radiolucent polymeric materials, which means that the implant can comprise one or more radio-opaque materials e.g. in the form of marking points so that the proportions of the implant can be seen more easier in X-ray exposures, as long as the ability to distinguish between bones and specifically new grown bones by radiography is not impaired. Thus in a preferred embodiment the body of the implant consists to ≥80% of one or more radiolucent polymeric materials, more preferably to ≥90% and most preferably to ≥95%.

"The body of the implant" as used herein refers to the structures consisting of the boundary layer, the scaffold zone, the tubular structures and the cavity, but specifically does not refer to the filling of the cavity.

The tubular structures and the cavity fillable with bone replacement material inside of the cage or the surgical implant is used for direct stimulation of bone growth and less for the stabilization of the entire implant. The mechanical stability of the surgical implant, the cage, is conferred by the boundary layer which completely or partly surrounds the implant, which is designed to withstand the high pressures of the spine and to prevent the sinking of the implant into the vertebral bone, so that the distance between two vertebral bodies, defined by the height of the boundary layer or the height of the implant respectively, can be maintained.

As already discussed above bone cells do not adhere very well to non-metallic bone-joining or bone-bridging implants that are made of polymeric materials. However, if polymeric materials are preferred, the ingrowth of new bone can be monitored by X-ray exposures.

Surprisingly, it was found that the inventive scaffold zone consisting of a plurality of tubular structures and a cavity fillable with bone replacement material promotes the ingrowth and adhesion of bone cells to implants substantially consisting of polymeric material. Each of the individual tubes running through the implant can suck or pull blood and cells by capillary forces into the whole tubular structure and thereby into the complete implant which promotes and accelerates formation of new bone within the bone-joining or bone-bridging implant.

As used herein the term "scaffold zone" refers to one or more tubular structures like two sets of parallel tubes, while the tubular structure consists of a plurality of tubes.

The cavity or cavities fillable with bone replacement material is essential to the invention and prevents that the bone cells just flow through the implant without attaching themselves. After the first bone cells attach themselves to the bone replacement material, they can start proliferating or they recruit further cells to the inside of the implant, respectively the tubular structure(s). Once initial cells are attached it is easier for further cells to attach and the implant is grown through from the inside.

The cavity can be filled with any bone replacement material or bone cement or artificial bone material suited for the use in a patient or with patient's own bone grafts or fine bone chips taken form patient's hip. Bone replacement material as used herein is a generic term comprising three major groups of materials:

The first group comprises polymeric bioresorbable materials. Suitable examples according to the invention are (l-lactic acid) [PLLA], poly(d l-lactic acid) [PDLLA], poly (glycolic acid) [PGA], poly(lactic-co-glycolic acid) [PLGA], poly(paradioxanone) [PDS], poly(dl-glycolic acid) [PDLGA], poly(propylene fumarate) [PPF], oligo (PEG fumarate) [OPF], poly(ethyleneglycol) [PEG], poly(caprolactone) [PCA], poly(hydroxybutyrate) [PHB], poly(hydroxy valerate) [PHV], poly (SA-HDA anhydride), poly (orthoesters), poly(phosphazenes), and copolymers of di-lactic acid and dl-glycolic acid.

The advantage of such bioresorbable materials is that the initial attachment of bone cells including proliferation and recruitment of further cells is promoted by the bioresorbable material, but afterwards when the bone replacement material is no longer needed it gets degraded giving way for further growth of bones through the implant. The rate of degradation doesn't have to be tightly controlled because the mechanical stability of the implant is not dependent on the bone replacement material. A subgroup may contain mineral blocks of animal origin.

The bone replacement material can be enriched with active substances like antibiotics, growth factors, adhesion molecules, silver, substances that promote the adhesion of bone cells and others. Thus according to the invention any osteoinductive substance can be used. In a preferred embodiment fibroblast growth factor (FGF) is added. Particularly preferred is the use of rhBMP-2 (Infuse®), a recombinant human bone morphogenetic protein capable of initiating bone growth in specific, targeted areas of the spine.

A second group comprises bioresorbable materials as listed for the first group or other biocompatible materials such as ceramic materials, enriched with human mesenchymal stem cells or other cells suitable as a germination point for the desired ossification. These mesenchymal stem cells can differentiate into bone cells either by themselves or by addition of a suitable agent. These differentiation procedures are known in the art.

The third group comprises bone cement. Bone cement are a form of bone replacement material. It is often provided as two-component materials. Bone cement consists of a powder (i.e., pre-polymerized PMMA and or PMMA or MMA co-polymer beads and or amorphous powder, radio-opacifier, initiator) and a liquid (MMA monomer, stabilizer, inhibitor). The two components are mixed and a free radical polymerization of the monomers occurs when the initiator is mixed with the accelerator. The bone cement viscosity changes over time from a runny liquid into a dough like state that can be safely applied and then finally hardens into solid hardened material.

According to the invention also combinations of materials from the aforementioned groups can be used.

The cavity inside the scaffold zone or inside the implant can be filled with bone replacement material, bone cement or artificial bone material before the implantation of the inventive implant. Thus the implant can be prefabricated and commercialized already with a filling of bone replacement material inside the cavity of the surgical implant.

In a further embodiment the filling of the cavity of the inventive implant with bone replacement material takes place immediately before implantation of the implant.

In a preferred embodiment the filling of the cavity of the inventive implant with bone replacement material, bone cement or artificial bone material takes place after implantation of the implant, i.e. inside the body. It is preferred that the filling occurs by means of microinvasive tools. However, normally the at least one cavity is filled by the physician just before the implantation.

Suitable for this purpose are all conventional tools for filling cavities, such as syringes, injection systems, catheter systems, tubing systems, pumping systems, jet systems, portioning systems, spoons, spatulas, pipettes, crushers, compactors, squeezing machines.

Thus the present application refers also to a method of loading the surgical implant, comprising the following step: a) Filling the at least one cavity of the surgical implant with a bone replacement material or bone cement or artificial bone material.

According to this method the bone replacement material can be selected from the group comprising polymeric bioresorbable materials, polymeric bioresorbable materials containing an osteoinductive agent, bioresorbable materials containing bone-forming cells and artificial bone material. The term "artificial bone material" as used herein is a subgroup of the bone replacement material and refers to any material which can be conferted to new bone under physiologic condition.

For this method it is preferred that the bone replacement material is a polymeric bioresorbable material containing an osteoinductive agent.

For this method it is even more preferred that this osteoinductive agent is rhBMP-2.

The filling of the inner cavity with at least one of the aforementioned materials thus serves for creating surfaces to which bone cells can adhere. Further, this filling serves for reducing the volume of the inner cavity in order to promote the through growth. This desired through growth and overgrowth is significantly improved by the special tubular structure running through the implant. This tubular structure enables the blood to run through the upper plane to the lower plane and because of the substantially horizontal tubes also from the outside of the implant to the inner cavity and vice versa. Thus bone cells can settle around the implant. By the inventive tubular structure bone cells can reach via the blood flow any site inside the implant so that the formation of new bone tissue doesn't occur only from the upper plane and/or the lower plane towards the center but also from the center of the implant towards the periphery.

Thus the present invention also refers to a kit which provides all materials necessary for such an implantation. This kit comprises at least one inventive surgical implant; and bone replacement material and/or bone cement and/or artificial bone material suitable to fill the cavity of the surgical implant. Such a kit comprises the surgical implant and bone replacement material and/or bone cement and/or artificial bone material in an amount sufficient to fill the at least one cavity of the surgical implant. Moreover such a kit may also comprise a carrier or a solid support which can be loaded with the bone replacement material or artificial bone material or may comprise a textile-like material which can be impregnated with the bone replacement material or artificial bone material. Moreover this kit may comprise an implantation device for inserting the inventive implant into the spinal column of the patient.

In another embodiment the kit comprises additionally at least one tool for filling the bone replacement material into the cavity of the surgical implant.

All bone replacement materials listed above can be used with different degrees of viscosity. Thus the bone replacement material can set immediately after filling into the cavity, it can set after some time, it can set only on application of an external energy source such as UV hardening, on cooling, on heating, or it may even remain in a semifluid or plastic state throughout the life time of the implant, respectively until being resorbed by the organism.

Thus according to the invention also substances can be added to the bone replacement material which allow for a controlled setting upon application of an external energy source.

It is known to a skilled person how to modify the viscosity and thus in most cases the setting conditions of the bone replacement material. One way to modify the viscosity consists in adding softening or hardening substances. One preferred additive for increasing the viscosity of the bone replacement material is polyvinyl pyrrolidone. It can be added in amounts up to 1 or 2% per volume.

The term viscosity refers to the dynamic viscosity $[\eta]$:

$$[\eta] = \frac{kg}{m \cdot s} = Pa \cdot s = \frac{Ns}{m^2}$$

Typical viscosity values for the bone replacement material (while not set) range from aqueous solutions (ca. 1 mPa·s), olive oil: $10^2$ mPa·s, honey ($10^3$ mPa·s), syrup ($10^5$ mPa·s) to bitumen ($10^9$ mPa·s). It is understood that the viscosity changes while setting or hardening.

The boundary layer which surrounds the implant gradually loses its supportive function ever the more the scaffold zone is grown through with bones. Therefore a fast and easy evaluation of the bone structure growing in the scaffold zone is desirable as a long-term stability is only obtained if the scaffold zone is grown through as completely as possible with endogenous bone cells.

FIG. 1 shows a top view of an inner cross section of an inventive surgical implant. In this embodiment the cavity is circular, but the cavity can have any desired shape and proportion. The cavity is preferably connected to most of the surrounding tubes and thereby with the surrounding tubular structure(s). Moreover, it is preferred that the tubes are arranged in a way that all tubes are interconnected, i.e. the entire tube-type structure could theoretically be filled through one opening of one tube with liquid such as blood. So preferably a three-dimensional interconnectivity of the entire structure is created.

The cavity can reach from one side of the implant to the other side of the implant. It is also possible that a part of the boundary layer is breached and the cavity is not completely enclosed by the cage material. The cavity can be split in two or more cavities of different size and proportions. Thus it is not necessary that the cavity is contiguous, but it is also possible that two or more cavities are filled with the same or different bone replacement material and are traversed by tubes or not independently from each other. Thus if two or more cavities exist, those cavities are all independent from each other regarding their properties, size, bone replacement material filling, traversing of tubes, enrichment with active substances and others. Consequently, in a further embodiment the intervertebral implant comprises more than one cavity.

The design of the tubes and the cavity themselves is not essential to the invention, but their presence. It is obvious to a skilled person, that too many openings and especially size and proportions of the cavity can affect the stability of the implant, so that a skilled person knows how to determine the number, size, location and proportions of the openings and of the cavity depending on the type of the implant. In order to improve the adhesion of bone cells further the inner surfaces of the tubular structure(s) and especially the surface of the bone replacement material can be structured by, for example, any mechanical, chemical or physical roughening. To suppress the growth of bacteria or other germs on the implant surface, it can be provided with antibiotics and the outer surface of the boundary layer for example can be provided with a drug eluting coating, in which agents such as antibiotics are stored and can be released continuously.

At the posterior or anterior side of the implant a centrally round recess may be located which serves to hold an implantation tool during implantation. This recess can penetrate the boundary layer (FIG. 3B) so that directly behind the recess the tubular structure starts. In a preferred embodiment the recess penetrates the boundary layer and directly behind the recess starts the cavity. This way the cavity can be filled conveniently with the bone replacement material.

The cavity can be filled either before insertion or after insertion of the implant in the human body. The cavity does not have to be filled completely and can also be filled only partially with bone replacement material. The surface of the bone replacement material can be structured in any way to enlarge the available surface area.

The inventive implants or cages are preferably made of one piece and have a defined scaffold structure, which supports the blood flow and a cavity filled with bone replacement material thus creating the best possible conditions for endogenous bone growth and have a boundary layer which is responsible for the stability at least as long as the newly formed bone cannot yet take over this function.

The term "one-piece surgical implants" refers only to the implant itself and not to any fasteners. Such implants can be screwed for example into the adjacent vertebral bodies. The used fasteners, for example screws are not taken into account when using the term "one-piece" and are referred to as accessories to the inventive surgical implant as well as the implantation tool. The inventive implants are thus made in accordance with this definition preferably in one-piece. Two-piece embodiments are also possible, wherein the inventive implants are made up of maximal three pieces, preferably of not more than two pieces, whereby the other parts generally relate to intended attachment means for the implant such as removable panels for mounting screws or hooks or fastening nails or the like, which usually are optional for the inventive implants.

In bone-joining or bone-bridging implants of the spine area as well as with the inventive implants, the contact planes of the implants are generally flat to the respective bone.

The contact planes of the cage is understood to be the surface, which comes into contact with the overlying vertebral body and the opposite surface of the cage, which comes into contact with the underlying vertebral body.

But the contact plane with the bone has not to be designed flat, as is the case with the intervertebral implants of the prior art, but can also have an asymmetrical form, as can be seen in FIG. 5. It is certainly more preferable, when the inner tubular structure extends slightly over the boundary layer in the direction of the overlying vertebral body as well as in the direction of the underlying vertebral body as will be described below in more detail. The part of the inner tubular structure extending over the boundary layer sinks or presses in the overlying or underlying vertebral body respectively and thus leads to an intended injury of the surface of these two vertebral bodies, whereby the growth of bones and the blood flow is further increased.

It isn't mandatory either that all vertical tubes start on the bone-contacting surface, i.e. in direct contact with the bone. Up to 30%, preferably up to 20% of all vertical tubes, can also start in one area of the implant that is not in direct contact with the bone, i.e. preferably these tubes start lower than or below the bone-contacting plane.

Furthermore, it is essential to the invention that the tubes of the inner tubular structure are interconnected. The vertical tubes are connected through the horizontal tubes and optionally in additional through openings while the horizontal tubes can optionally connect with each other through openings, wherein each horizontal tube has preferably at least one opening to an adjacent horizontal tube.

As already described above the entire tubular structure could theoretically be filled through one opening of one tube with liquid. However, to achieve the best result it is preferred that at least 20%, preferably 30%, more preferably 40%, even more preferably 50% of the tubes open into the cavity. This way it is ensured that enough blood and bone cells come into contact with the bone replacement material.

Furthermore, implants according to the invention are preferred where the honeycomb structure, i.e. the inner tubular structure, rises slightly over the essentially flat bone-contacting plane. Especially, if the honeycomb structure of the implant protrudes over a border or solid frame or boundary layer, the advantage of a high surface friction and therefore a very good anchorage is given. At the same time the low thickness of the honeycomb walls gives rise to the possibility of mechanical movements which promotes growth stimulation of the bone.

Moreover, it is preferred that the openings in the inner tubular structure are arranged in such a way that the entire structure permits micro-movements, preferably friction-movements. Such movements are possible when the single vertical tubes are connected by wedge-shaped longitudinal cuts in the lateral wall areas along the longitudinal axis of the vertical tubes. Thus, the individual tube walls can be shifted against each other according to the thickness of the wedge-shaped openings, so that micro-movements are possible.

As outlined above it is preferred for the majority of embodiments that the inventive surgical implant is made of a metallic material to allow a monitoring of the ingrowth of bone cells into the implant via x-ray spectrometry and radiography through the horizontal tubes.

Surprisingly, it showed that it is feasible by the inventive implants to monitor the through growth of the implant by means of x-rays via the horizontal tubes.

Herein, a radiography is taken from the implant, respectively the patient, in such an angle so that a fraction of the x-ray beams passes through the horizontal tubes or at least a group of horizontal tubes. Therefore it is essential that the horizontal tubes crossing the inner cavity take a straight way through the anterior boundary layer as well as through the posterior boundary layer so that an x-ray beam can pass through the entire implant via a single horizontal tube without being refracted and not only through the anterior part or the posterior part of the boundary layer. In the latter case the beam would eventually end on the opposite side of the inner cavity (i.e. on the opposite inner wall of the boundary layer) on solid material which is again radiopaque, thus counteracting the x-ray monitoring. In case the implant has an inner cavity which is filled with bone grafts or fine bone chips or bone replacement material or bone cement or artificial bone material, the X-ray spectrum or the radiography can be performed in a way that the measurement is made through the horizontal tubes (7") which do not run through the inner cavity.

The presence of more than one group of parallel horizontal tubes allows for taking radiographies from different angles by performing the radiography through the respective groups of horizontal tubes. Herein, the lumen of the tubes appears dark on the radiography, as long as no bone has been formed inside these tubes. As soon as the ossification starts the interior of the tubes will appear grayish, according to the progress. The solid and radiopaque portions of the implant appear in white. Therefore it is possible to monitor the through growth via the horizontal tubes. Radiographies can be taken from different angles and combined in order to create an overview of the progress of ossification. The differentiation between hollow tubes, ossified tubes and solid material is straight forward in general. FIG. 8 shows the inventive surgical implant from a lateral view. The white sections shows the radiopaque material of the surgical implant, i.e. of the boundary layer. The dark or black sections are the horizontal tubes through which the x-ray beams could pass and expose the x-ray film at the other end of the implant. When new bone tissue has been built inside the tubes they appear grayish since the x-rays can't pass anymore freely. Bone is not as radiopaque as the metal of the boundary layer.

The inventive surgical implants have an inner cavity that can be filled with bone replacement material, bone cement or autologous bone chips. According to the indication and to the preferences of the physician different fillings of this cavity are favored. If the cavity is filled with bone replacement material then this bone replacement material should preferably not contain an opacifier. Only without an opacifier the newly built bone tissue can be differentiated from the bone replacement material. Herein, a radiography is taken through the horizontal tubes in which the bone replacement material without an opacifier appears dark, as being widely x-ray transparent, and the newly built bone appears light gray. So the current degree of ossification of the implant can be monitored. If the physician uses cancellous bone material for filling the cavity this cancellous bone material appears dark to dark gray via the horizontal tubes, as the cancellous bone mass is widely x-ray transparent. New bone formed in the inner cavity of the implant, however, then appears light to light gray and thus can be differentiated from the cancellous bone mass. If the physician uses, however, cortical bone for filling the cavity of the surgical implant the cortical bone appears light on radiographies taken via the horizontal tubes and thus can't be differentiated from newly built bone tissue. In order to detect the through growth of the inventive surgical implant by means of x-rays when the inner cavity is filled with cortical bone material, the inventive surgical implants have two types (7' and 7") of horizontal tubes (7). One species of horizontal tubes (7') runs through the boundary layer and exits on the interior surface of the boundary layer. The other species (7") runs exclusively through the boundary layer and does not cross the inner cavity. They exit at the opposite side of the boundary layer. Preferentially, this type of tubes has no direct opening or direct cross-connection with the inner cavity. In FIG. 7 such horizontal tubes (7") are shown that are running through the tip of the implant towards the back side of the boundary layer. When filling the inner cavity this tube species remains free through their entire length so that it can be determined by radiography to which degree a through growth of these tubes has occurred. This advantage isn't offered by any conventional metal cage. It is important for radiographies that the x-ray device is positioned in such a way that the radiography can be taken through the tubes. This isn't a technical challenge anymore nowadays. On these radiographies radiopaque materials such as the metal of the surgical implant appear light to white, newly built bone and cortical bone appears light gray or light gray to light, cancellous bone and bone replacement material dark gray or dark gray to dark and free tubes allowing an unimpeded passage of the x-ray beam appear dark to black. Therefore according to the invention the surgical implant can be also made of metal. This applies in particular for the scaffold zone with the tubular structure. According to the invention also hybrid implants made of a polymeric material and metal can be used. In these embodiments the percentage of weight of metal versus polymer can range between 0.01% and 99.99%, preferably from 0.1% to 99%, more preferably from 1% to 90% and most preferably 30% to 70%. For these embodiments all specifications on structures, materials, coatings, sizes and combinations with therapeutic agents made for the polymeric embodiments apply in the same manner.

The implants of the present invention and the detection of new bone formation within the implants of the present invention can be shown best in FIGS. 8, 11, 12, 13, and 14.

FIGS. 8 and 13 are the radiographs of two implants of the present invention with empty horizontal tubes and consequently also with empty vertical tubes. The horizontal tubes are displayed dark or black since the X-ray beams can freely pass through the horizontal tubes. The metal of the cage is radiopaque and appears white or very light.

FIG. 11 is a radiograph of the cage of FIG. 8 which is almost completely filled with new bone. The new bone within the horizontal tubes appear light gray and can be clearly distinguished from the radiopaque metal material of the cage. It has to be kept in mind that the physician does normally have a radiograph of the empty cage like shown in FIG. 8 and thus clearly knows the size, number and location of the single horizontal tubes. In the radiograph of FIG. 11 it seems that only two horizontal tubes are not completely filled with new bone. This is the tube almost in the middle of the cage and the tube in the second column from the right side of the cage and in the middle of that column. These two horizontal tubes are still displayed dark so that they seem to be still open.

FIG. 12 is a radiograph of another inventive cage where the bone has just started to grow through that cage from the top and the bottom towards the center of the cage. From the radiograph of FIG. 12 it is evident that only the middle of the upper first row of horizontal tubes and the lowest row of horizontal tubes is filled with new bone while all other tubes are still in black which indicates that they are still empty. After two to three weeks after implantation such a radiograph can be expected.

FIG. 13 is a radiograph of another inventive cage where none of the horizontal tubes is filled neither with new bone nor with bone grafts or fine bone chips or bone replacement material or bone cement or artificial bone material. All horizontal tubes are displayed in black so that the X-ray beams could freely pass through these tubes.

FIG. 14 is a radiograph of the cage of FIG. 13 wherein a group of horizontal tubes is filled with a bone replacement material. The bone replacement material without an opacifier is widely x-ray transparent, but of course not completely x-ray transparent so that X-ray beams can almost unhindered pass through such horizontal tubes filled with bone replacement material (without opacifier). The group of horizontal tubes filled with bone replacement material consists of the following horizontal tubes: fifth row from the bottom, tube 4 from the left side; fourth row from the bottom, tubes 3 and 4 from the left side; third row from the bottom, tubes 4 to 8 from the left side; second lowest row, all 8 tubes and lowest row, all 8 tubes.

Thus the present inventive cages allow the detection of the degree, location and velocity of new bone formation and the conversion of bone replacement material or artificial bone material or autologous bone chips or autologous bone grafts or cancellous bone mass into new bone, since all such materials have a distinguishable x-ray transparency.

Only cortical bone mass used as filling material for the cage cannot be distinguished from newly formed bone. However in such cases the degree and velocity of the formation of new bone and the conversion of the cortical bone mass into new bone can be detected by X-ray spectra recorded through the horizontal tubes (named herein as tubes 7") which do not cross the inner cavity and which do not have a direct opening to the inner cavity and which run straight through the boundary layer from one side to the other. These tubes (7") remain empty although the inner cavity of the cage is filled with cortical bone mass. Thus only newly formed bone can close or seal these tubes (7") so that the appearance of these horizontal tubes (7") indicates if new bone was formed therein are not at the time the radiograph was taken. If all such tubes (7") are filled with new bone it can be concluded that the cortical bone mass within the inner cavity of the cage was completely or almost completely converted to new bone.

Suitable materials for the inventive cage implant are medical steal, titanium, titanium oxide, chromium, vanadium, tungsten, zirconium, oxidized zirconium, molybdenum, hafnium, gold, platinum, rhodium, niobium, lead, cobalt-chromium, tantalum, as well as alloys of these metals and biodegradable materials such as magnesium, zinc, calcium, iron as well as polymeric materials such as fiber-reinforced polymers (glass/carbon fibers in a suitable matrix) chitosan, hepara, polyhydroxybutyrate (PHB), polyglyceride, polylactide and copolymers thereof.

Suitable metals include, but are not limited to medical stainless steel, titanium, chromium, vanadium, tungsten, molybdenum, gold, magnesium, iron, zinc, calcium, lithium, sodium, potassium, aluminium, scandium, zirconium, niobium, tantalum, silicon, manganese, iron, cobalt, nickel, copper, zinc, gallium, yttrium, ruthenium, rhodium, palladium, silver, indium, tin, lanthanum, cerium, praseodymium, neodymium, promethium, samarium, europium, gadolinium, terbium, dysprosium, holmium, erbium, thulium, ytterbium, lutetium, rhenium, platinum, lead and/or at least one metal salt with a cation selected from the group comprising $Li^+$, $Na^+$, $Mg^{2+}$, $K^+$, $Ca^{2+}$, $Sc^{3+}$, $Ti^{2+}$, $Ti^{4+}$, $V^{2+}$, $V^{3+}$, $V^{4+}$, $V^{5+}$, $Cr^{2+}$, $Cr^{3+}$, $Cr^{4+}$, $Cr^{6+}$, $Mn^{2+}$, $Mn^{3+}$, $Mn^{4+}$, $Mn^{5+}$, $Mn^{6+}$, $Mn^{7+}$, $Fe^{2+}$, $Fe^{3+}$, $Co^{2+}$, $Co^{3+}$, $Ni^{2+}$, $Cu^+$, $Cu^{2+}$, $Zn^{2+}$, $Ga^+$, $Ga^{3+}$, $Al^{3+}$, $Si^{4+}$, $Y^{3+}$, $Zr^{2+}$, $Zr^{4+}$, $Nb^{2+}$, $Nb^{4+}$, $Nb^{6+}$, $Mo^{4+}$, $Mo^{6+}$, $Tc^{2+}$, $Tc^{3+}$, $Tc^{4+}$, $Tc^{5+}$, $Tc^{6+}$, $Tc^{7+}$, $Ru^{3+}$, $Ru^{4+}$, $Ru^{5+}$, $Ru^{6+}$, $Ru^{7+}$, $Ru^{8+}$, $Rh^{3+}$, $Rh^{4+}$, $Pd^{2+}$, $Pd^{3+}$, $Ag^+$, $In^+$, $In^{3+}$, $Ta^{4+}$, $Ta^{5+}$, $W^{4+}$, $W^{6+}$, $Pt^{2+}$, $Pt^{3+}$, $Pt^{4+}$, $Pt^{5+}$, $Pt^{6+}$, $Au^+$, $Au^{3+}$, $Au^{5+}$, $Sn^{2+}$, $Sn^{4+}$, $Pb^{2+}$, $Pb^{4+}$, $La^{3+}$, $Ce^{3+}$, $Ce^{4+}$, $Gd^{3+}$, $Nd^{3+}$, $Pr^{3+}$, $Tb^{3+}$, $Pr^{3+}$, $Pm^{3+}$, $Sm^{3+}$, $Eu^{2+}$, $Dy^{3+}$, $Ho^{3+}$, $Er^{3+}$, $Tm^{3+}$, $Yb^{3+}$, as well as alloys of aforesaid metals. In addition to the aforementioned metals and metal salts small amounts of non-metals, carbon, sulfur, nitrogen, oxygen and/or hydrogen may be present.

In preferred metal alloys metals such as aluminium, medical steel and/or gold can be added.

In some embodiments it is preferred that the metal is bioresorbable, respectively biodegradable. This group includes lithium, sodium, magnesium, aluminum, potassium, calcium, scandium, titanium, vanadium, chromium, manganese, iron, cobalt, nickel, copper, zinc, gallium, silicon, yttrium, zirconium, niobium, molybdenum, ruthenium, rhodium, palladium, silver, indium, tin, lanthanum, cerium, praseodymium, neodymium, promethium, samarium, europium, gadolinium, terbium, dysprosium, holmium, erbium, thulium, ytterbium, lutetium, tantalum, tungsten, rhenium, platinum, gold, lead. It has shown that for a variety of applications it is advantageous to fill the cavity or the cavities inside the scaffold zone with a textile-like material, impregnated with the aforementioned substances suitable for filling the cavity. Such a textile-like material can be a physiologically acceptable felt material, medical cellulose, bandaging material, wound insert, compress, sponge or medical textile.

In some embodiments it is preferred that this textile-like material is bioresorbable. Thus with some time after implantation the textile-like material is degraded, respectively resorbed while the bone replacement material remains.

It is preferred that the textile-like material can adjust to any surfaces, i.e. it can follows the surface contours of a cavity inside the scaffold zone. It is also possible that such a textile-like material fills up to the entire volume of the cavity or the cavities.

It is understood that the term textile-like materials not necessarily refers to only a material consisting of one piece, but also to plurality of pieces. These pieces can be made of the same or of differing materials.

It is preferred that such a textile-like material is highly impregnable with the bone replacement material. If the textile-like material is bioresorbable the remaining bone replacement material should be able to fill a considerable part of a cavity inside the scaffold zone. It may also happen that after biodegradation of the textile-like material some air pockets are generated inside the bone replacement material. If the textile-like material is not biodegradable the impregnated textile-like material will remain inside the cavity throughout the life time of the implant. It is understood by the term "biodegradable" or "bioresorbable" that these materials are degraded or will have been degraded within a period of 6 month up to 24 months, preferably within 9 to 21 months, more preferably within 12 to 18 months and most preferably between 14 and 16 months under physiological conditions.

Suitable materials for biodegradable textile-like materials are polyacrylic acid, polyacrylate, polymethyl methacrylate, polybutyl methacrylate, polyisobutyl methacrylate, polyacrylamide, polyacrylnitrile, polyamide, polyetheramide, polyethyleneamine, polyimide, polycarbonate, polycarbourethane, polyvinylketone, polyvinylhalogenide, polyvinylidenhalogenide, polyvinylether, polyvinyl aromatics, polyvinyl ester, polyvinylpyrollidone, polyoxymethylene, polyethylene, polypropylene, polytetrafluoroethylene, polyurethane, polyolefin elastomer, polyisobutylene, EPDM gums, fluorosilicone, carboxymethylchitosan, polyethyleneterephtalate, polyvalerate, carboxymethylcellulose, cellulose, rayon, rayon triacetate, cellulose nitrate, cellulose acetate, hydroxyethyl cellulose, cellulose butyrate, cellulose acetate-butyrate, ethylvinylacetate copolymer, polysulfone, polyethersulfone, epoxy resin, ABS resins, EPDM gums, silicone pre-polymer, silicone, polysiloxane, polyvinyl halogen, cellulose ether, cellulose triacetate, chitosane, chitosan derivatives, polymerisable oils, polyvalerolactones, poly-e-decalacton, polylactide, polyglycolide, co-polymers of polylactide and polyglycolide, poly e caprolactone, polyhydroxy butyric acid, polyhydroxybutyrate, polyhydroxyvalerate, polyhydroxybutyrate-co-valerate, poly(1,4-dioxan-2,3-dione), poly(1,3-dioxan-2-one), poly-para-dioxanone, polyanhydride, polymaleic acid anhydride, polyhydroxy methacrylate, polycyanoacrylate, polycaprolacton dimethylacrylate, poly-β-maleic acid, polycaprolactonbutyl acrylate, multiblock polymers made of oligocaprolactonediol and oligodioxanondiol, polyetherester-multi-block polymers made of PEG and poly(butyleneterephthalate), polypivotolactone, polyglycolic acid trimethylcarbonate, polycaprolactone-glycolide, poly(γ-ethylglutamate), poly(DTH-iminocarbonate), poly(DTE-co-DT-carbonate), poly(bisphenol A-iminocarbonate), polyorthoester, polyglycolic acid trimethyl-carbonate, polytrimethylcarbonate, polyiminocarbonate, polyvinylic alcohols, polyester amides, glycolidized polyesters, polyphosphoesters, polyphosphazenes, poly[p-carboxyphenoxy)propane], polyhydroxypentaic acid, polyethylene oxide-propylene oxide, soft polyurethanes, polyurethanes with amino acid rests in the backbone, polyether esters, polyethylene oxide, polyalkenoxalates, polyorthoesters, carrageenans, starch, collagen, protein-based polymers, polyamino acids, synthetic polyamino acids, zein, modified zein, polyhydroxyalkanoates, pectic acid, actinic acid, fibrin, modified fibrin, casein, modified casein, carboxymethylsulphate, albumin, hyaluronic acid, heparan sulphate, heparin, chondroitin sulphate, dextrane, cyclodextrine, co-polymers made of PEG and polypropyleneglycol, gum arabic, guar, or other gum resins, gelatine, collagen, collagen-N-hydroxysuccinimide, lipids, lipoids, polymerisable oils and their modifications, co-polymers and mixtures of the aforementioned substances.

Suitable materials for non-biodegradable or biostable textile-like materials are polymethyl methacrylate, polybutyl methacrylate, polyacrylamide, polyacrylonitriles, polyamides, polyetheramides, polyethyleneamine, polyimides, polycarbonates, polycarbourethanes, polyvinylketones, poly(vinyl halogenide)s, poly(vinylidene halogenide)s, polyvinylethers, polyvinylic aromatics, polyvinylic esters, polyvinylpyrollidones, polyoxymethylenes, polyethylene, polypropylene, polytetrafluoroethylene, polyurethanes, polyolefin elastomers, polyisobutylene, fluorosilicones, carboxymethyl chitosan, polyethyleneterephtalate, polyvalerate, carboxymethyl cellulose, cellulose, rayon, rayon triacetates, cellulose nitrate, cellulose acetate, hydroxyethyl cellulose, cellulose butyrate, cellulose acetate-butyrate, ethylvinylic acetate-co-polymeres, polysulfones, epoxy resins, ABS resins, EPDM gums, silicones such as polysiloxanes, polyvinylic halogens and co-polymers, cellulose ether, cellulose triacetate, chitosan and co-polymers and/or mixtures thereof.

Medical Cellulose

Polyhydroxybutyrate and cellulose derivatives, chitosan derivatives as well as collagen, polyethylene glycol, polyethylene oxide and polylactides are preferred materials for medical celluloses as textile-like materials. Calcium alginate products interwoven with sodium carboxymethyl cellulose are used preferably if alginates are used as wound covers. SeaSorb Soft from the company Coloplast is to be given as an example.

The products Tabotamp® and Spongostan® from the company Johnson and Johnson have to be mentioned in particular. These products are produced of regenerated cellulose by controlled oxidation.

If compresses are to be impregnated with the bone-replacement material in particular sterile gauze compresses of 100% cotton have to be used herein. Examples are the product lines Stericomp® und Askina®.

If medical cellulose is used it is preferred that it has a cellulose content of more than 90%.

Trevira® products are preferred if medical textiles are used.

Sponges

The medical sponges are bioresorbable implants with a spongy porous structure.

Preferred materials for medical sponges are collagen, oxidized cellulose, chitosan, thrombin, fibrin, chitin, alginate, hyaluronic acid, PLGA, PGA, PLA, polysaccharides and globin.

If medical sponges are used it is preferred that they have a collagen content of more than 90%.

Thus the present application also refers to a textile-like material suitable for being impregnated with bone replacement material for being inserted into the cavity inside the scaffold zone of a surgical implant.

Finally the present invention is directed to a method for making an X-ray spectrum or a radiograph by adjusting the X-ray apparatus in a way that the X-ray beams can pass through at least a group of horizontal tubes and conducting the X-ray measurement through such tubes. This method is useful to detect the degree, area, completeness and velocity of through growth of new bone through the implant or the conversion of bone replacement material or artificial bone material or autologous bone chips or autologous bone grafts or cancellous bone mass into new bone.

EXAMPLES

Figure 1:
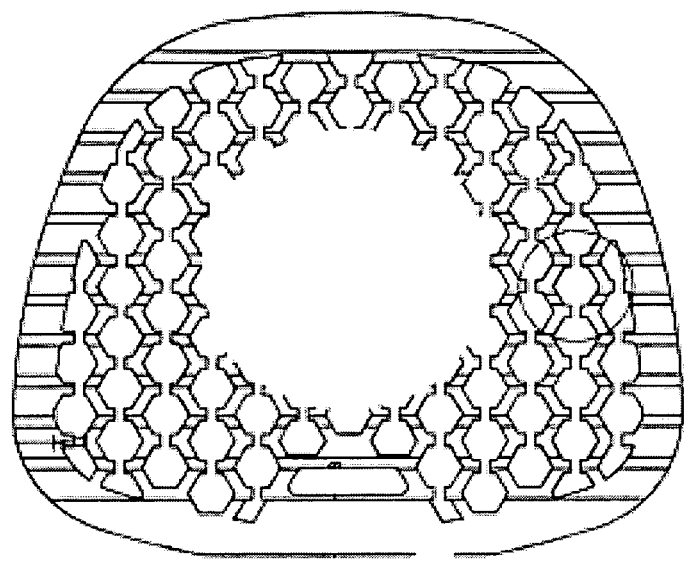
FIG. 1 shows a top view of an inner cross section of an inventive surgical implant with a circular cavity in the middle of the implant and openings to the upper plane and the lower plane of the implant. Thus the cavity is like a bore hole through the implant from the upper plane to the lower plane along the longitudinal axis of the spinal column.
Figure 2:
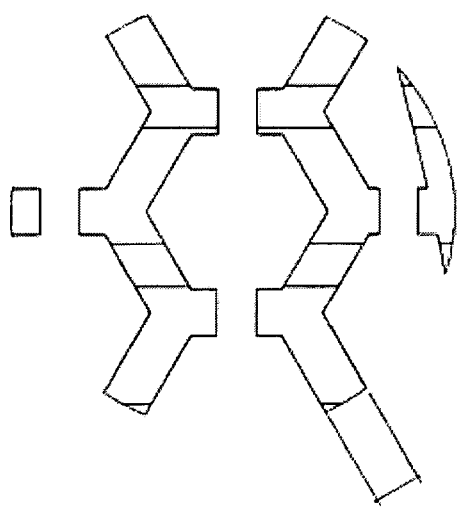
FIG. 2 shows the tubular structure in the surgical implant, which is an enlargement of the encircled area in FIG. 1.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Example 1: Cage

Example 1 relates to a PEEK cage, especially a cervical cage with a longitudinal diameter of 14 mm and a transverse diameter of 12 mm and a height of 8 mm. The Cage is nearly oval and the longitudinal diameter is understood to be the maximum diameter and the transverse diameter is understood to be the smallest diameter.

The cage is made of PEEK with an at least 1.1 mm thick boundary layer and an upper and lower flat plane for contact with the respective vertebral bodies. The boundary layer surrounds the anterior and the posterior side of the implant while the lateral sides do only have an upper and lower frame or ring of the boundary layer. In the middle of the lateral sides the inner tubular structure starts. At the posterior side of the implant a centrally round recess is located, which serves to hold an implantation tool during implantation and through which the cavity is filled with artificial bone material (PMMA).

Inside the cage a honeycomb structure of tubes is formed with hexagonal walls. The vertical tubes extend in a straight line from the top of the bone-contacting surface to the opposite lower vertebral contacting flat surface. In the middle of the implant is a circular cavity completely filled with bone cement. Per cm² bone-contacting surface about 34-42 tubes are available.

The vertical tubes have a diameter of 870-970 μm specified as the distance between two opposing parallel walls.

The vertical tubes are also interconnected through openings in the tube walls.

The openings have a wedge-shaped structure so that the tube walls can be shifted laterally only by the thickness of the notches against each other, which leads to an increased stability of the implant. The opening has a diameter of 60 μm.

The cage has also horizontal tubes perpendicular to the vertical tubes. The horizontal tubes are also formed with hexagonal walls and have the same diameter as the vertical tubes. The horizontal tubes run straight from one lateral side of the implant to the opposite side. The horizontal tubes are not connected with openings to each other. The margin area from where no horizontal tubes start is 1.5 cm wide and forms a square frame around the area where the horizontal tubes start.

Example 2: Cage

Example 2 refers to a cage, especially a cervical cage with a longitudinal diameter of 14 mm and a transverse diameter of 12 mm and a height of 8 mm. The Cage is nearly oval and the longitudinal diameter is understood to be the maximum diameter and the transverse diameter is understood to be the smallest diameter.

The cage is made of titanium and has a thickness of the boundary layer of 5 mm for contacting the respective vertebral body.

Inside the boundary layer (1) there is a tubular structure of round tubes. The horizontal tubes (7) have all a diameter of 1.5 mm. The horizontal tubes (7") that don't run through the inner cavity are straight and in parallel so that x-ray beams can pass along these tubes (7"). There are two groups of vertical tubes. The boundary layer (1) is traversed from its upper plane (3A) up to its lower plane (3B) with round vertical tubes (5') having a larger diameter of 1.0 mm. In the periphery of the boundary layer (1) close to the inner surface (9) or close to the outer surface (8), there are smaller round vertical tubes (5") with a diameter of 0.5 mm that are placed between the outer surface (8) and the larger tubes (5') and also between the inner surface (9) and the larger tubes (5').

Per cm² upper plane (3A) of the boundary layer (1) as well as per cm² lower plane (3B) of the boundary layer (1) there are between 30 and 100 vertical tubes (5). Per cm² outer surface (8) of the boundary layer (1) as well as per cm² inner surface (9) of the boundary layer (1) there are between 34 and 42 horizontal tubes (7). In the periphery of the boundary layer (1) there extend between 10 and 20 horizontal tubes (7") that run exclusively inside the boundary layer (1) and don't cross the inner cavity (2) or don't end on the inner surface (9) of the boundary layer (1).

At the thinnest site between the horizontal tubes (7) the wall thickness amounts still to 0.2 mm. At the thinnest site between the vertical tubes (5) the wall thickness amounts still to 0.15 mm.

The volume of the cage material (such as titanium) is 708 mm³ and the total surface area is 3198 mm² so that the ratio of volume of cage material to total surface area is 221 μm.

Example 3: TLIF Cage

Figure 5:
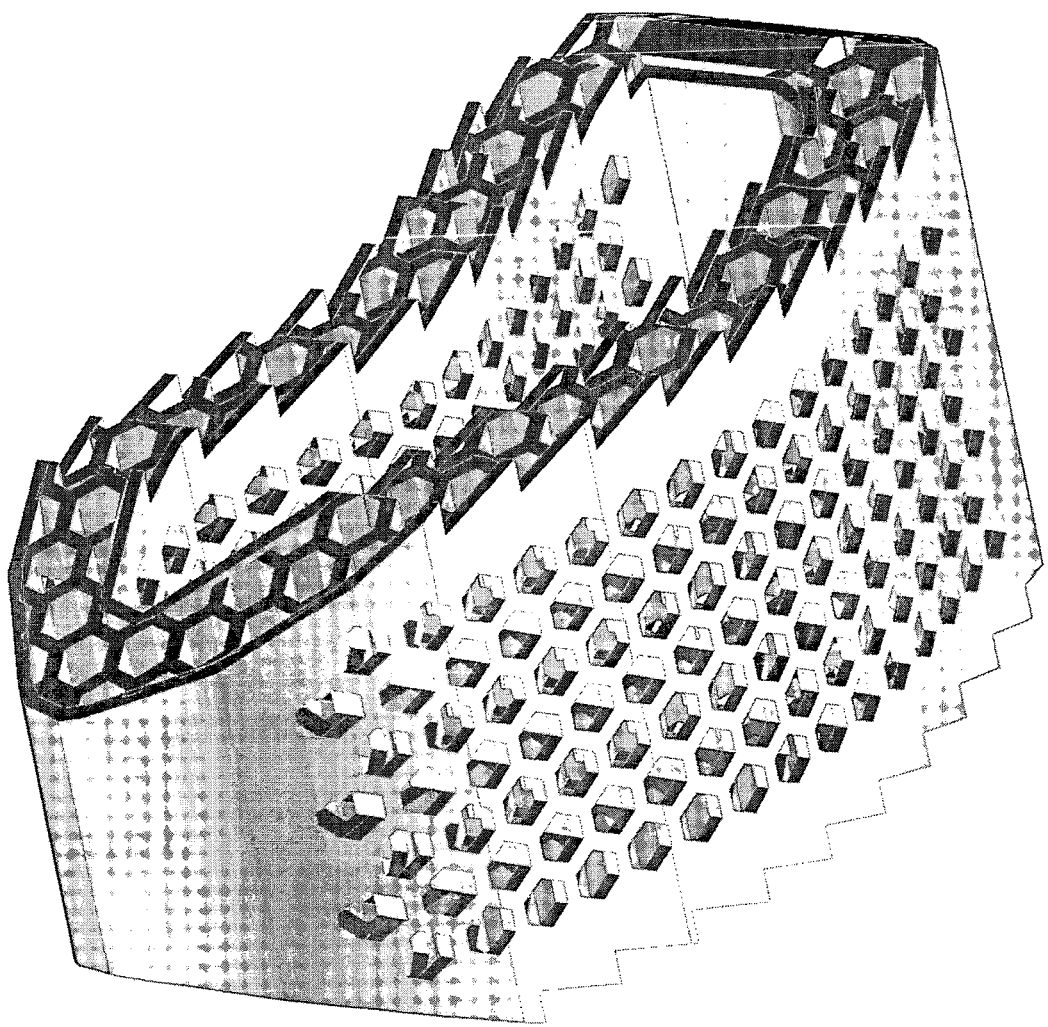
FIG. 5 shows a perspective view of another embodiment of the inventive surgical implant, a so-called TLIF cage. The cage shape serves only as an example and isn't mandatory. The boundary layer of the implant surrounds the inner cavity and is traversed by vertical and horizontal tubes. The implant consists of a physiologically acceptable material, in particular a metal or a metal alloy. The bone contacting surface is rippled in this embodiment in order to stimulate bone growth and to achieve a better anchoring at the vertebral body.

An embodiment of the inventive surgical implant is now described in regard of FIG. 5. This figure shows an inventive surgical implant with a particular tubular structure. The boundary layer (1) builds the implant and surrounds the inner cavity (2). The boundary layer (1) has an upper plane (3A) that is jagged in the present example in order to achieve an improved anchoring at the adjacent vertebral body, and a lower plane (3B) that is likewise jagged. The boundary layer (1) has a thickness of 3 mm. At the ventral side the surgical implant is tapered into a tip out of anatomical reasons. At the dorsal side the surgical implant has a flattened back side (4). The vertical tubes (5) run from the upper plane (3A) of the boundary layer (1) straight and in parallel throughout the boundary layer (1) up to the lower plane (3B) of the boundary layer (1). The vertical tubes (5) have a hexagonal shape and a diameter of 0.4 mm at its full size, i.e. if the vertical hexagonal tubes (5) are not cut off in the periphery of the boundary layer (1). Of all vertical tubes (5) 80% to 85% have this full size, i.e. they are not cut off in the periphery of the boundary layer (1) and have said diameter of 0.4 mm. Per cm² upper plane and lower plane the boundary layer (1) has between 150 and 200 vertical tubes. The wall thickness (6) of the vertical tubes amounts to 0.2 mm. The vertical tubes (5) are interconnected via the horizontal tubes (7). The horizontal tubes (7) run straight and in parallel throughout the boundary layer (1). There are two species of horizontal tubes (7), such horizontal tubes (7') that run from the exterior surface (8) of the boundary layer (1) to the interior surface (9) of the boundary layer, and those horizontal tubes (7") that don't cross the inner cavity (2) and run exclusively throughout the boundary layer (1). The horizontal tubes (7') are characterized in that they run from the inner surface (9) of the boundary layer (1) to the exterior surface (8) of the boundary layer (1). The horizontal tubes (7") are characterized in that they run from one side of the boundary layer (1) to the opposite side of the boundary layer (1) without crossing the inner cavity (2).

The horizontal tubes (7) have a hexagonal shape and a diameter of 2.0 mm in their full size, i.e. if the horizontal hexagonal tubes (7) are not cut off in the periphery of the boundary layer (1). Of all horizontal tubes 96% have this full size, i.e. they aren't cut off in the periphery of the boundary layer (1) and have said diameter. Per cm² outer surface (8) and inner surface (9) the boundary layer (1) has between 5 and 15 horizontal tubes. The wall thickness (10) of the horizontal tubes amounts to 0.5 mm.

The volume of the cage material (such as medical stainless steel) is 406 mm³ and the total surface area is 1958 mm² so that the ratio of volume of cage material to total surface area is 207 μm.

Example 4: ALIF Cage

Figure 6:
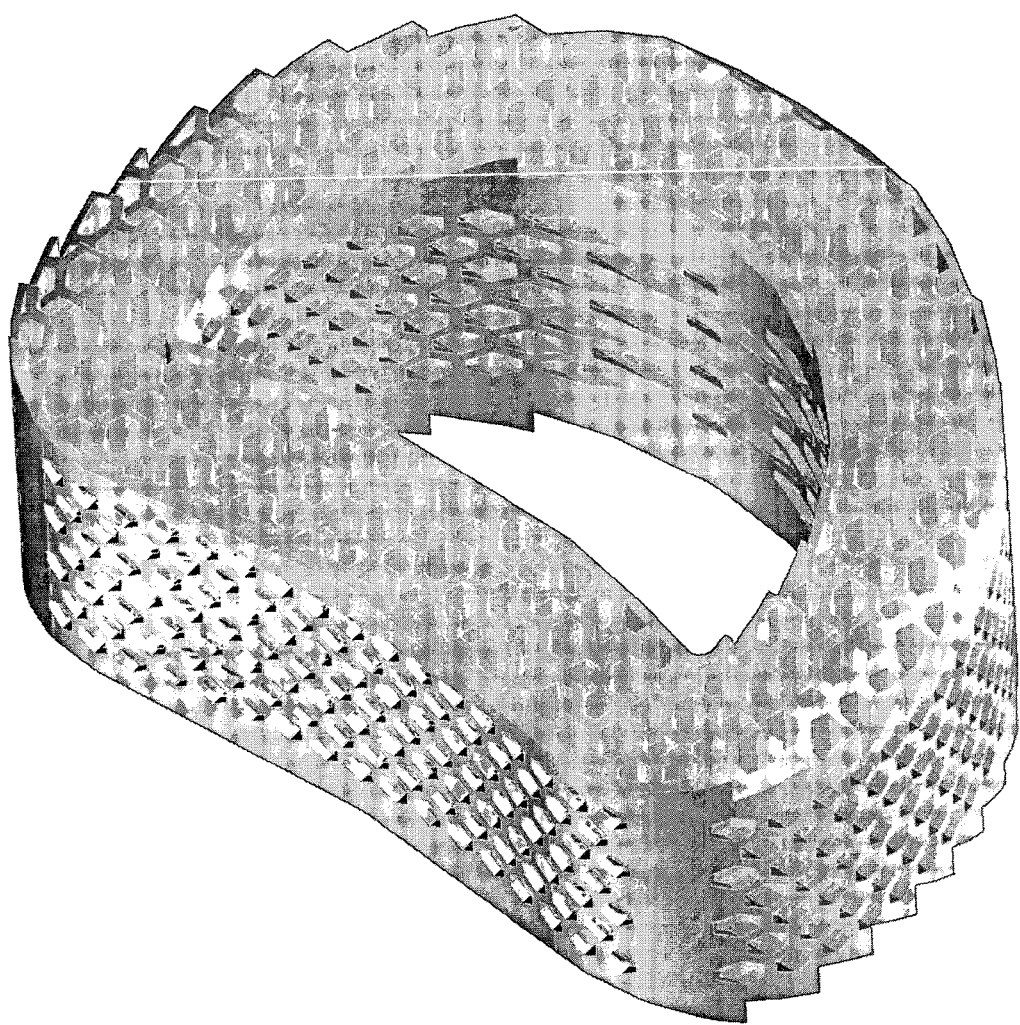
FIG. 6 shows a perspective view of a further inventive surgical implant, a so-called ALIF cage.
Figure 7:
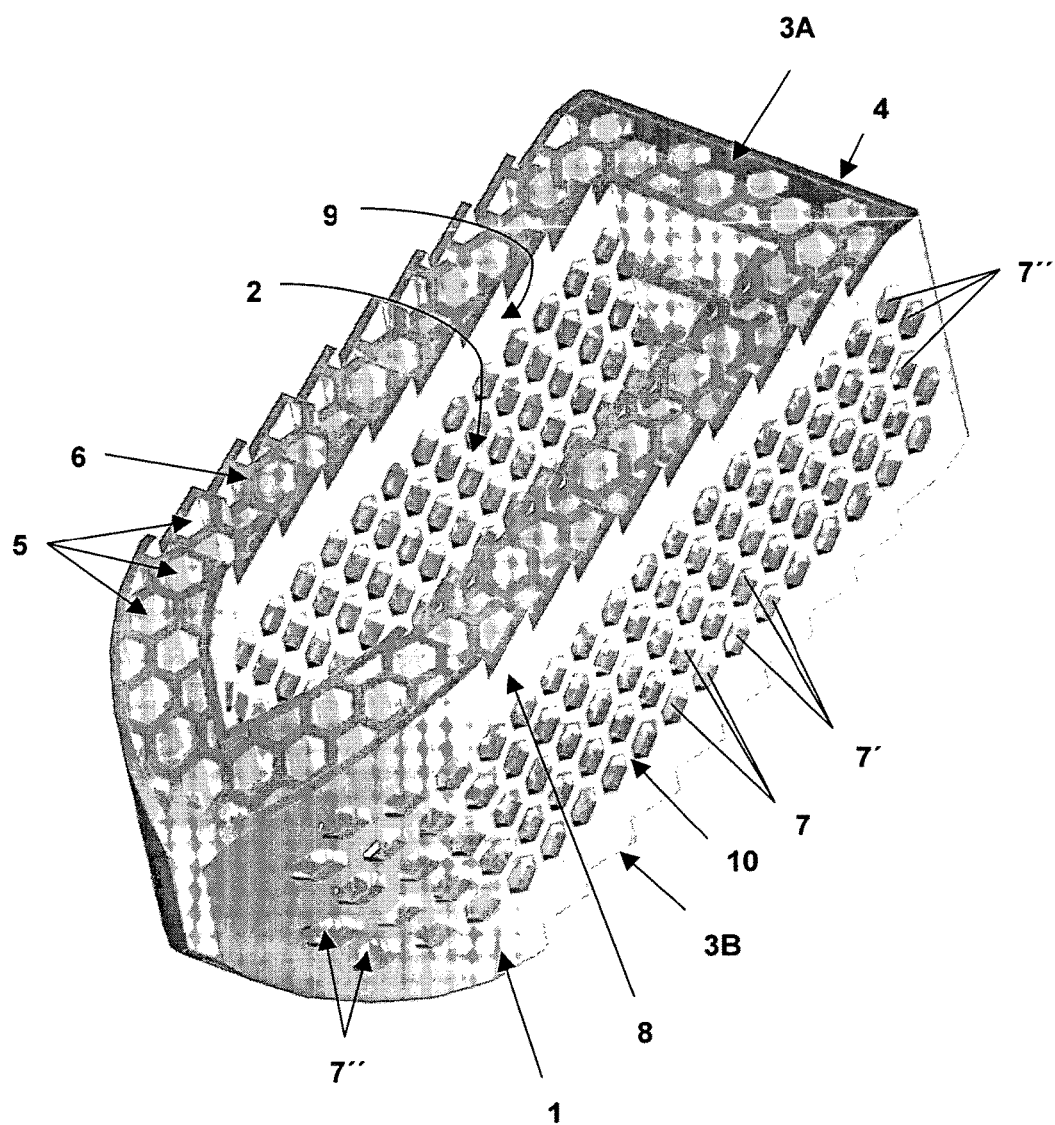
FIG. 7 shows a perspective view of another inventive surgical implant, a so-called PLIF cage. The implant is built by the boundary layer (1) that has an upper plane (3A), a lower plane (3B) and a back side (4) and it surrounds the inner cavity (2). The boundary layer (1) has the inventive tubular structure of vertical tubes (5) and horizontal tubes (7 or 7' or 7") wherein the horizontal tubes (7 or 7' or 7") run from the outer surface (8) to the inner surface (9) of the boundary layer (1) and have a minimal wall thickness (10). Also the vertical tubes (5) have a minimal wall thickness (6). From these 87 horizontal tubes in total 10 horizontal tubes (7") run exclusively through the boundary layer (1) and 77 horizontal tubes (7') run through the boundary layer (1) and the inner cavity (2). All horizontal tubes (7) have a hexagonal shape.
Figure 8:
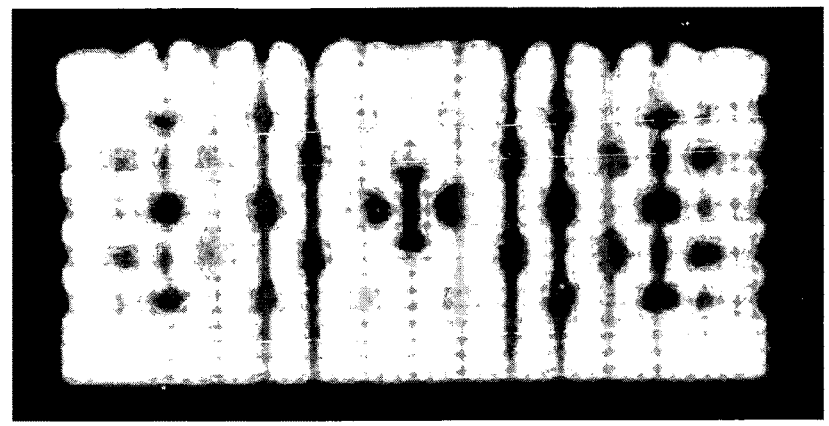
FIG. 8 shows a radiography of an inventive surgical implant in which the dark sections represent the horizontal tubes and the light sections the radiopaque cage material.
Figure 9:
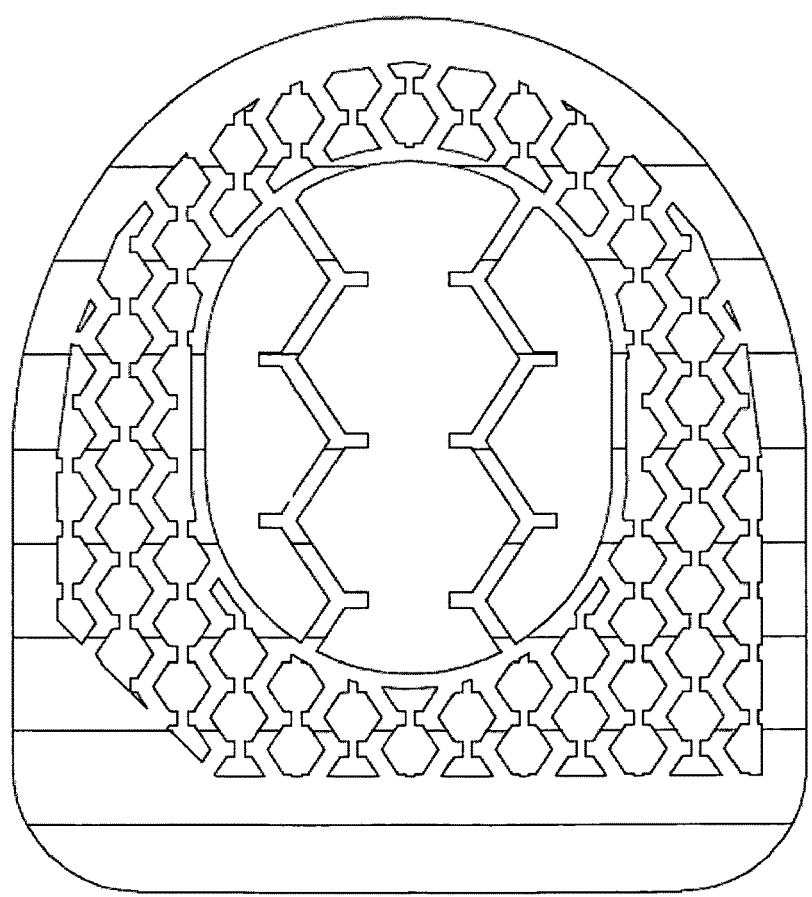
FIG. 9 shows the top view of a further variant of the inventive surgical implant wherein the inner cavity (2) is separated by two partitions. The two partitions are not interconnected and display a zigzag shape, i.e. they have the same shape as the tube walls of the boundary layer. Moreover, the two partitions also have the openings of the horizontal tubes so that an x-ray beam can pass along a horizontal tube (7') through the boundary layer (1), the corresponding opening in the first partition, the corresponding opening in the second partition and the horizontal tube in the opposite boundary layer section. Fine openings can be seen between the vertical tubes (5) that interconnect the vertical tubes.
Figure 10:
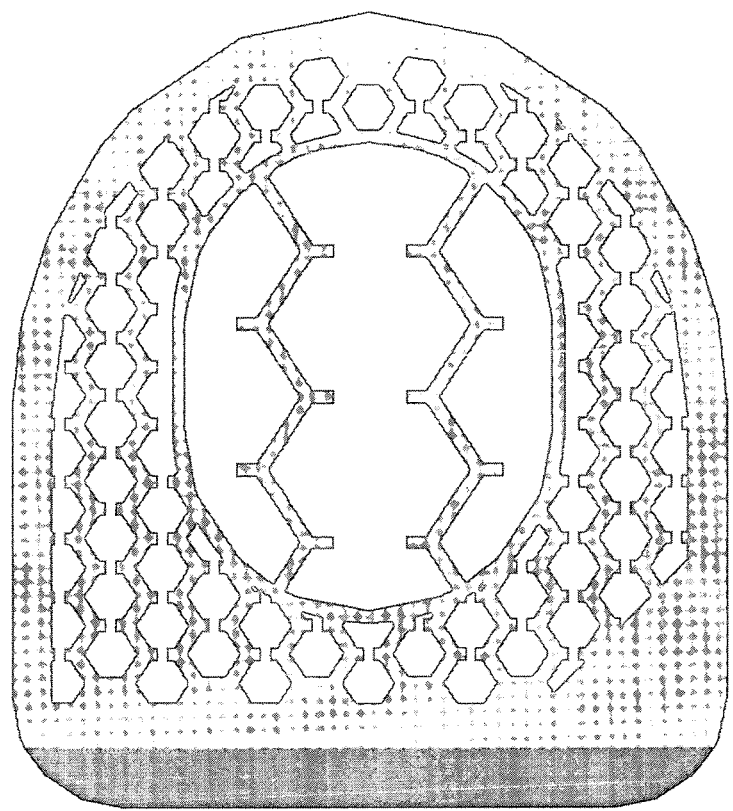
FIG. 10 shows a similar view as FIG. 9 in another display mode.
Figure 11:
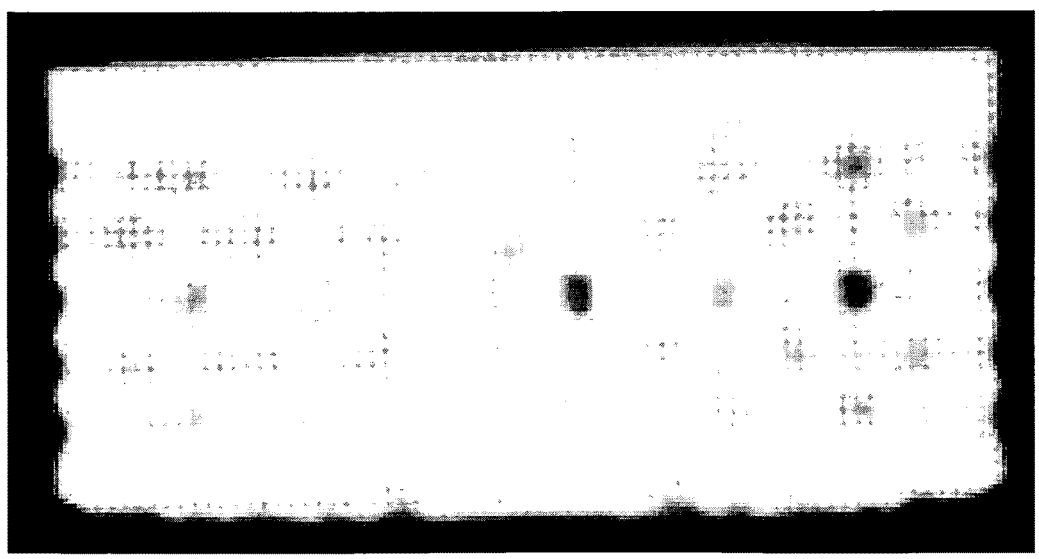
FIG. 11 shows a radiography of the surgical implant of FIG. 8 which is almost completely through grown with new bone. The dark sections visible in FIG. 8 disappeared which indicates that all horizontal tubes are filled with bone. Only one tube in the center of the cage and another tube in the middle right side of the cage seem not to be filled completely with new bone. The light sections are still the radiopaque cage material which is titanium in the present case.
Figure 12:
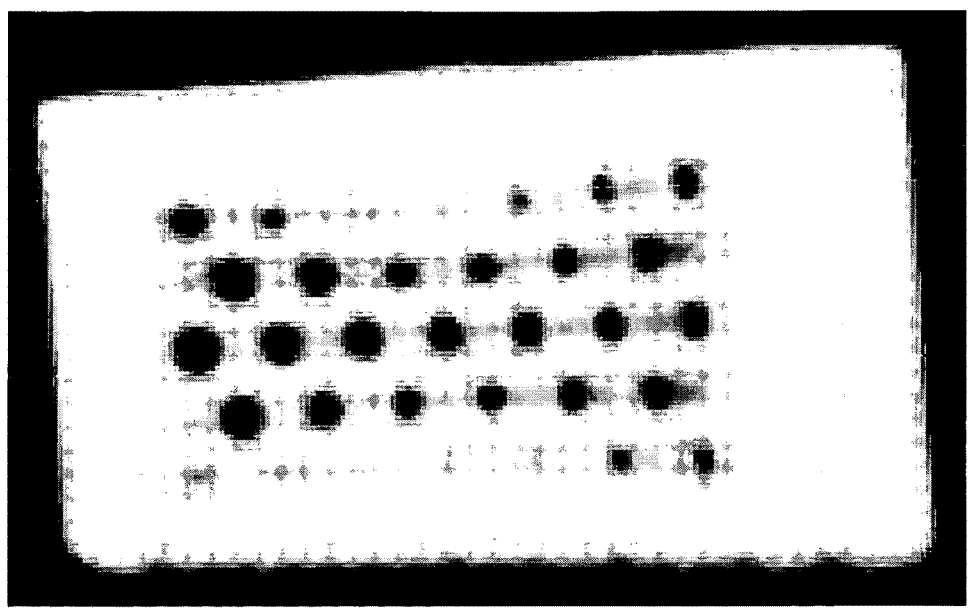
FIG. 12 shows a radiography of another embodiment of a cage of the present invention where the new bone has just started to grow into the cage. The tubes in the middle part of the cage are still empty and thus appear dark or black. The tubes at the upper section and of the lower section of the cage appear light grey which indicates that new bone has started to grow into these tubes. Thus this figure clearly indicates that the new bone starts growing from the upper plane and simultaneous from the lower plane of the implant through the vertical tubes into the horizontal tubes in direction to the center of the implant.
Figure 13:
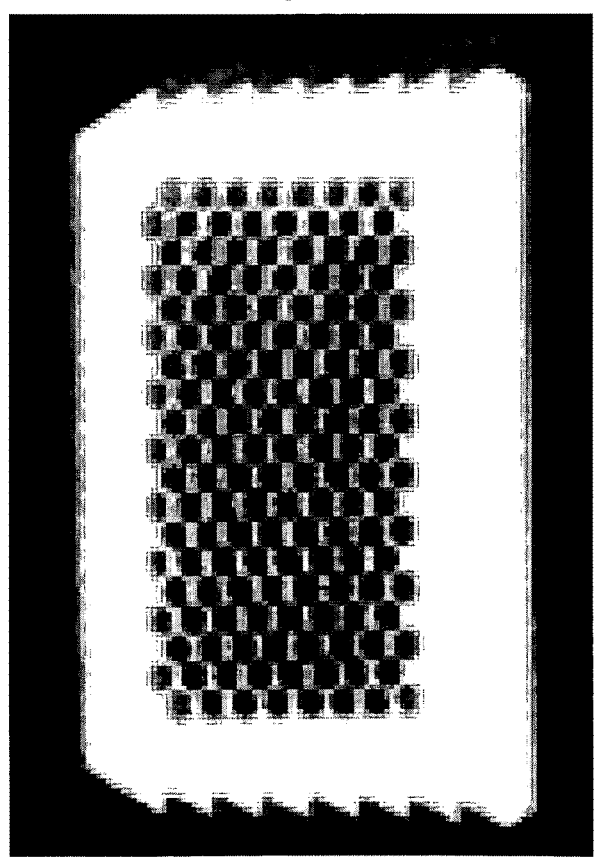
FIG. 13 shows a radiography of another embodiment of a cage of the present invention wherein all tubes are empty. Similar to FIG. 8, the horizontal tubes are black and the cage material which is titanium appear white or light.
Figure 14:
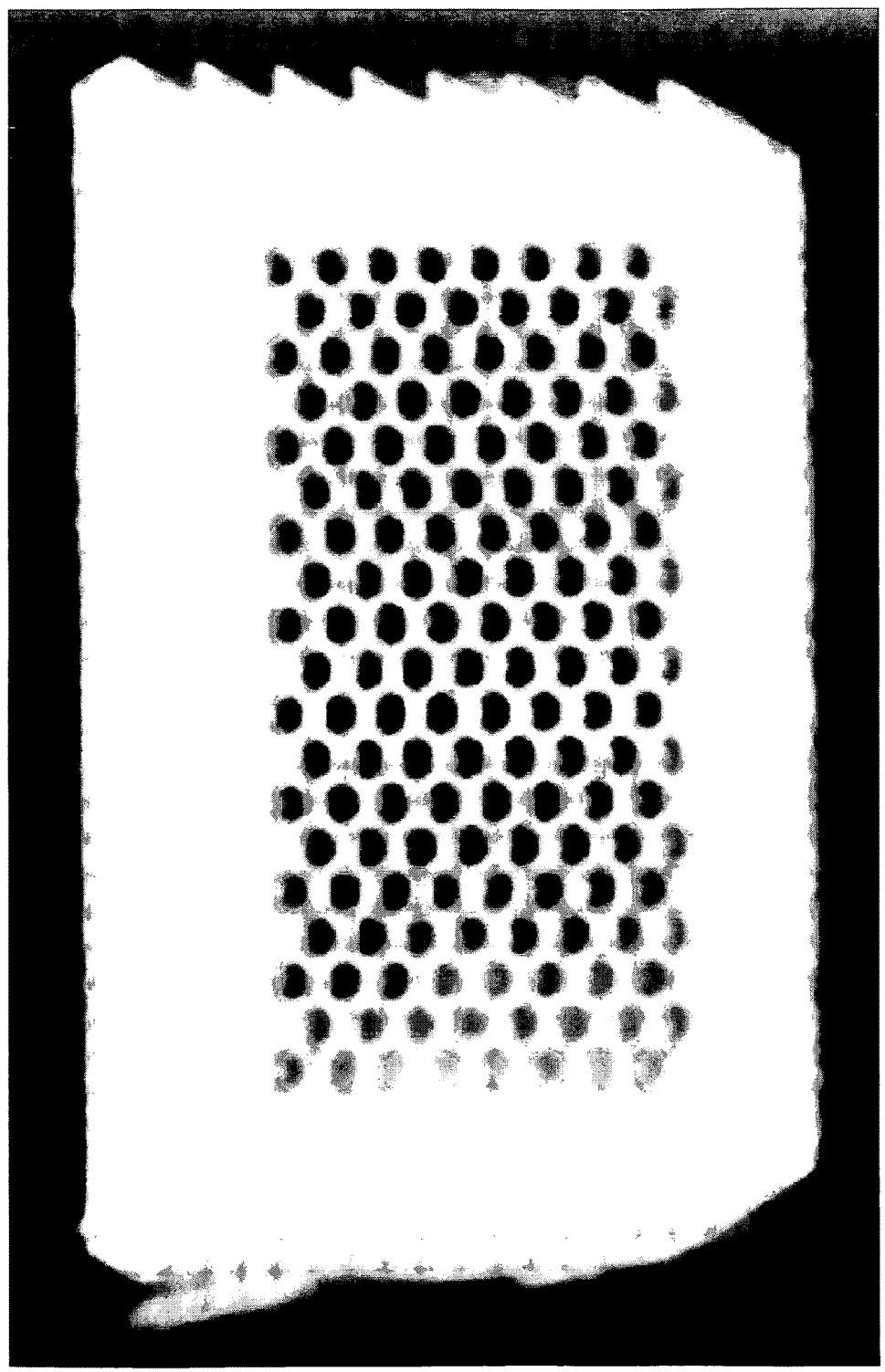
FIG. 14 shows a radiography of the cage of FIG. 13 which is partly filled with bone replacement material in the lower part of the cage. The lower two lines of horizontal tubes are filed, since they appear gray to dark gray, i.e. the lowest line and the second lowest line of horizontal tubes are completely filled with bone replacement material. In the third lowest line the 5 horizontal tubes from the right side to the middle are also filled with bone replacement material while the three tubes at the left side in the line are empty and thus appear black or dark. Moreover two horizontal tubes are filled with bone replacement material in the fourth lowest line which are the third and fourth tube from the left side of the cage and only one horizontal tube in the fifth lowest line is filled with bone replacement material. That tube is the fourth tube from the left side which is also the fifth tube from the right side of the cage. Thus, the X-ray spectra shown in FIGS. 8, 11, 12, 13, and 14 allow to distinguish between radiopaque cage material, empty tubes, tubes filled with bone and tubes filled with bone replacement material.

An embodiment of the inventive surgical implant is now described in regard of FIG. 6. This figure shows an inventive surgical implant with a particular tubular structure. The surgical implant is formed by the boundary layer (1) that surrounds the inner cavity (2). The boundary layer (1) has an upper plane (3A) that is jagged in the present example in order to ensure a better anchoring at the adjacent vertebral body, and a lower plane (3B) that is likewise jagged. The boundary layer (1) has a thickness of 7.0 mm. The inventive surgical implant has the typical heart shape of an ALIF cage. The vertical tubes (5) run from the upper plane (3A) of the boundary layer (1) straight and in parallel throughout the boundary layer (1) to the lower plane (3B) of the boundary layer (1). The vertical tubes (5) have a hexagonal shape and a diameter of 1.8 mm in their full size, i.e. if they are not cut off in the periphery of the boundary layer (1). Of all vertical tubes (5) 65% to 75% have this full size, i.e. they aren't cut off in the periphery of the boundary layer (1) and have said diameter of 1.8 mm. Per cm² upper plane and lower plane the boundary layer (1) has between 15 and 30 vertical tubes. The wall thickness (6) of the vertical tubes amounts to 0.3 mm. The vertical tubes (5) are interconnected via the horizontal tubes (7). The horizontal tubes (7) extend straight and in parallel throughout the boundary layer (1). There are two species of horizontal tubes (7), such horizontal tubes (7') that extend from the outer surface (8) of the boundary layer (1) to the inner surface (9) of the boundary layer (1), and those horizontal tubes (7") that don't cross the inner cavity (2) but run through the boundary layer (1) exclusively. The horizontal tubes (7') are characterized in that they run from the inner surface (9) of the boundary layer (1) to the exterior surface (8) of the boundary layer (1). The horizontal tubes (7") are characterized in that they run from one side of the boundary layer (1) to the opposite side of the boundary layer (1) without crossing the inner cavity (2).

The horizontal tubes (7) have a hexagonal shape and a diameter of 2.0 mm in their full size, i.e. if the horizontal hexagonal tubes (7) are not cut off in the periphery of the boundary layer (1). Of all horizontal tubes 96% have this full size, i.e. they aren't cut off in the periphery of the boundary layer (1) and have said diameter. Per cm² outer surface (8) and inner surface (9) the boundary layer (1) has between 2 and 20 horizontal tubes. The wall thickness (10) of the horizontal tubes amounts to 0.4 mm.

The volume of the cage material (such as titanium) is 507 mm³ and the total surface area is 2371 mm² so that the ratio of volume of cage material to total surface area is 214 μm.

Example 5: Cage

Figure 3A:
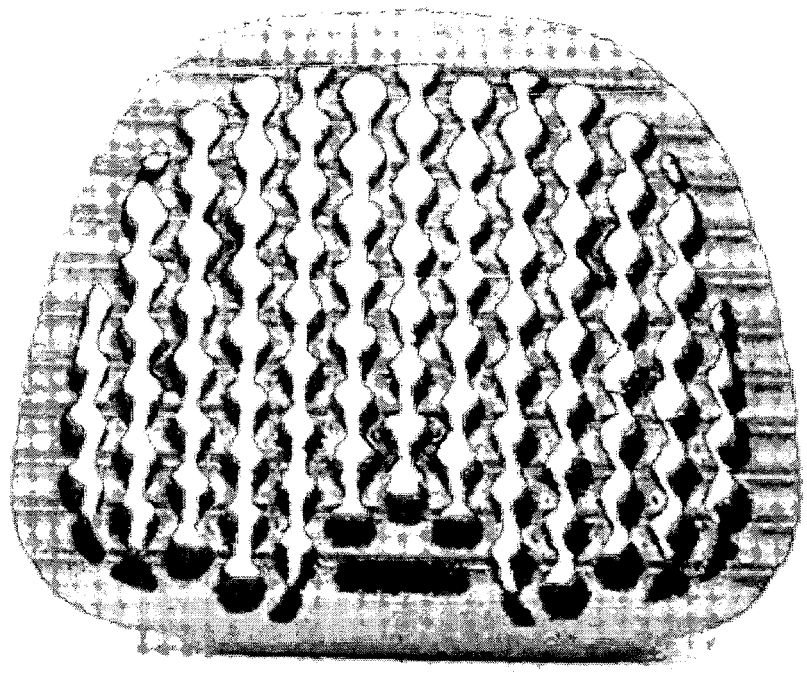
FIG. 3A shows a side view of an inventive surgical implant with a serrated top and serrated bottom. The teething is located in the honeycomb structure and in the boundary layer and serves to stabilize the position of the implant between the vertebral bodies after implantation. The horizontal tubes are not shown in FIG. 3A since it is a top view of the implant. The longitudinal cuts in the walls of the vertical tubes are shown clearly so that zig-zag walls remain which form within their bulges the vertical tubes. The zig-zag walls also allow micro movements which stimulate the formation of new bone. This implant does not have a defined cavity or volume fillabe with bone grafts or fine bone chips or bone replacement material or bone cement or artificial bone material. However the complete tubular structure or a group of vertical tubes could be partly or completely filled with bone grafts or fine bone chips or bone replacement material or bone cement or artificial bone material. A technical drawing of the embodiment of FIG. 3A is shown in FIG. 3B.
Figure 3B:
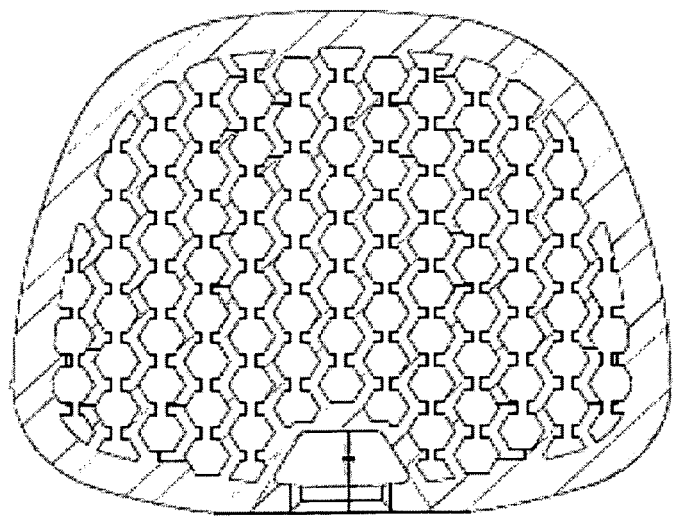
FIG. 3B is the technical drawing of the embodiment shown in FIG. 3A. Shown is the top view of the implant with the hexagonal or sexangular vertical tubes. Also shown is at the front side of the implant the part for inserting the implantation device. Not shown are the horizontal tubes which are also present in this embodiment. Clearly shown are the zig-zag walls forming the vertical tubes between these walls the thickness of the walls and the location and thickness of the longitudinal cuts in the walls of the vertical tubes.
Figure 3C:
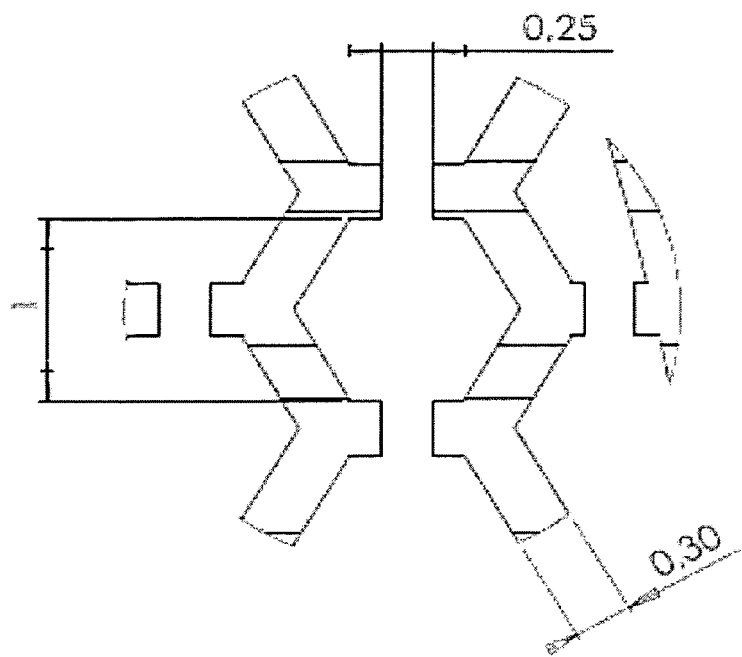
FIG. 3C shown an enlargement of a section of the tubular structure of the implant shown in FIG. 3B. Shown is one complete hexagonal vertical tube, the adjacent vertical tubes only partly. Moreover the diameter of the vertical tube is indicated as 1 mm. The walls are shown surrounding the vertical tube while the walls have a thickness of 0.30 mm and two longitudinal cuts in the walls of the vertical tubes located opposite to each other are shown which have a thickness of 0.25 mm. A tubular structure consisting of such hexagonal vertical tubes (and also hexagonal horizontal tubes which are not shown) guarantees capillary forces which suck blood and bone cells into the implant while the angled shape of the tubes advantages the adhesion of bone cells and the formation of new bone and the longitudinal cuts connect the vertical tubes to each other and allow the so formed zig-zag walls to perform micro movements which promote the formation of new bone.
Figure 4:
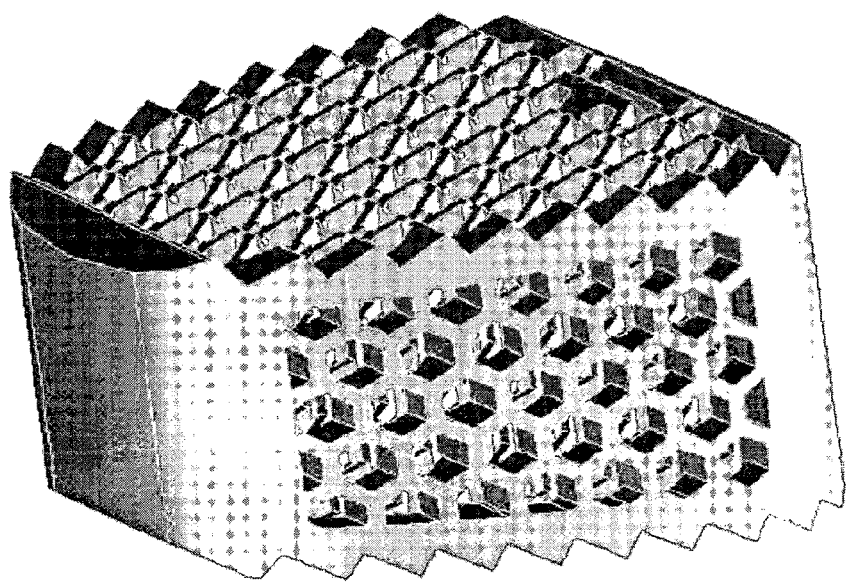
FIG. 4 shows an implant according to the present invention with the tubular structure consisting of a plurality of hexagonal vertical tubes and a plurality of hexagonal horizontal tubes which run straight through the implant so that X-ray beams can pass through the implant by passing through the horizontal tubes.

An embodiment of the inventive surgical implant is now described in regard of FIGS. 3A to 3C. These figures show an inventive surgical implant with a particular tubular structure. This surgical implant does not have an inner cavity and consists completely of the tubular structure while only the edges, a back of the implant and the front part where the implantation device is inserted are solid and do not comprise tubes. The implant has an upper plane (3A) for contacting the upper vertebral body and a lower plane (3B) for contacting the lower vertebral body.

The vertical tubes (5) run from the upper plane (3A) of the implant straight and in parallel throughout the implant to the lower plane (3B) of the implant. The vertical tubes (5) have a hexagonal shape and a diameter of 1.0 mm in their full size, i.e. if they are not cut off in the periphery of the implant. The implant has in total 104 vertical tubes (5), while 25 vertical tubes do not have their full size, because they are cut off in the periphery of the implant and 79 vertical tubes do have their full size. Thus of all vertical tubes (5) 76% have the full size, i.e. they aren't cut off in the periphery of the implant. The wall thickness (6) of the vertical tubes (5) amounts to 0.3 mm. Moreover in one line from dorsal to ventral the vertical tubes are connected to each other by longitudinal cuts which have a breadth of 0.25 mm. Due to the longitudinal cuts in the walls of the vertical tubes (5) zig-zag walls extending from the ventral side of the implant to the dorsal side are formed which can perform micro movements in order to stimulate bone formation.

Moreover the implant comprises 20 horizontal tubes (7) arranged in two lines of 10 horizontal tubes (7) one line upon the other running straight through the implant from one lateral side to the opposite lateral side of the implant so that X-ray beams can pass through these horizontal tubes (7) thereby passing through the implant. Also these horizontal tubes (7) have a hexagonal shape and all of them have a diameter of 1.0 mm in their full size, i.e. none of the horizontal hexagonal tubes (7) is cut off in the periphery of the implant. The wall thickness (10) of the horizontal tubes amounts to 0.3 mm. The horizontal tubes (7) are not interconnected to each other by longitudinal cuts or any other cuts into the walls of the horizontal tubes (7). However these horizontal tubes (7) run through or cross the vertical tubes (5).

The volume of the cage material (such as titanium) is 607 mm³ and the total surface area is 2785 mm² so that the ratio of volume of cage material to total surface area is 218 μm.

The invention claimed is:

1. A radiopaque intervertebral metal implant for fusion of two bridged vertebral bodies comprising:
an upper plane for contacting an upper vertebral body;
a lower plane for contacting a lower vertebral body;
a tubular structure formed by a plurality of tubes for the fusion of the two bridged vertebral bodies, the plurality of tubes comprises vertical tubes and horizontal tubes, wherein the vertical tubes run from the upper plane to the lower plane and the horizontal tubes run in a substantially horizontal direction throughout one side of the intervertebral implant straight to the opposite side of the intervertebral implant thereby interconnecting the vertical tubes;

the horizontal tubes of the tubular structure are parallel to each other or are grouped into groups of parallel horizontal tubes so that X-ray spectra or radiographs are conductable through the horizontal tubes, and wherein all surfaces of the intervertebral metal implant have a roughness of 6.0 Ra to 8.5 Ra.

2. The radiopaque intervertebral metal implant according to claim 1, further comprising at least one cavity in the center of the implant extending from the upper plane to the lower plane, and a boundary layer surrounding the at least one cavity.

3. The radiopaque intervertebral metal implant according to claim 2, wherein the boundary layer has a thickness of 1.5 mm to 10.0 mm.

4. The radiopaque intervertebral metal implant according to claim 2, wherein the at least one cavity is filled with a bone replacement material selected from polymeric bioresorbable materials, polymeric bioresorbable materials containing an osteoinductive agent, bioresorbable materials containing bone-forming cells or materials which are converted to new bone under physiologic conditions.

5. The radiopaque intervertebral metal implant according to claim 1, further comprising two, three, four, five or six cavities.

6. The radiopaque intervertebral metal implant according to claim 5, wherein between 10% and 90% of the horizontal tubes terminate at one of the cavities.

7. The radiopaque intervertebral metal implant according to claim 1, wherein the intervertebral implant has a porosity of at least 75%.

8. The radiopaque intervertebral metal implant according to claim 1, wherein a ratio of a volume of a solid implant material to a total implant surface area is between 200 μm and 230 μm.

9. The radiopaque intervertebral metal implant according to claim 1, wherein the vertical tubes of the tubular structure extend substantially along a longitudinal axis of a spinal column.

10. The radiopaque intervertebral metal implant according to claim 1, wherein the tubes have a dimension of 250 μm to 2,000 μm.

11. The radiopaque intervertebral metal implant according to claim 1, wherein the upper plane and the lower plane of the implant have at least 80 tubes per $cm^2$.

12. The radiopaque intervertebral metal implant according to claim 1, wherein the vertical tubes and/or the horizontal tubes don't change their inner diameter on their way through the implant.

13. The radiopaque intervertebral metal implant according to claim 1, wherein the implant is manufactured in one continuous piece.

14. The radiopaque intervertebral metal implant according to claim 1, wherein the implant is selected from the group consisting of cervical cages, thoracic cages, lumbar cages, artificial intervertebral disks and implants for the fusion of natural and artificial vertebrae.

15. The radiopaque intervertebral metal implant according to claim 1, wherein a ratio of a volume of a material of the implant to a volume of the tubes ranges from 10 vol. %:90 vol. % to 20 vol. %:80 vol. %.

16. The radiopaque intervertebral metal implant according to claim 1, wherein the metal implant is a titanium implant.

17. A radiopaque intervertebral metal implant for fusion of two bridged vertebral bodies comprises:
an upper plane for contacting an upper vertebral body;
a lower plane for contacting a lower vertebral body;
at least one cavity in the center of the implant extending from the upper plane to the lower plane, wherein the at least one cavity is surrounded by a boundary layer with a tubular structure comprising vertical tubes and horizontal tubes;
wherein the vertical tubes run from the upper plane to the lower plane; and
the horizontal tubes run in a substantially horizontal direction throughout one side of the intervertebral implant straight to the opposite side of the intervertebral implant thereby interconnecting the vertical tubes, the horizontal tubes are parallel to each other or are grouped into groups of parallel horizontal tubes so that X-ray spectra or radiographs are conductable through the horizontal tubes, and wherein all surfaces of the intervertebral metal implant have a roughness of 6.0 Ra to 8.5 Ra.

18. The radiopaque intervertebral metal implant according to claim 17, wherein the boundary layer surrounds the at least one cavity completely on the upper plane and the lower plane.

19. The radiopaque intervertebral metal implant according to claim 17, wherein the at least one cavity comprises two, three, four, five or six cavities.

20. The radiopaque intervertebral metal implant according to claim 17, wherein the boundary layer has a thickness of 1.5 mm to 10.0 mm.

21. The radiopaque intervertebral metal implant according to claim 17, wherein the intervertebral implant has a porosity of at least 75%.

22. The radiopaque intervertebral metal implant according to claim 17, wherein a ratio of a volume of a solid implant material to a total implant surface area is between 200 μm and 230 μm.

23. The radiopaque intervertebral metal implant according to claim 17, wherein the vertical tubes of the tubular structure extend substantially along a longitudinal axis of a spinal column.

24. The radiopaque intervertebral metal implant according to claim 17, wherein between 10% and 90% of the horizontal tubes terminate at the at least one cavity.

25. The radiopaque intervertebral metal implant according to claim 17, wherein the at least one cavity is filled with a bone replacement material selected from polymeric bioresorbable materials, polymeric bioresorbable materials containing an osteoinductive agent, bioresorbable materials containing bone-forming cells or materials which are converted to new bone under physiologic conditions.

26. The radiopaque intervertebral metal implant according to claim 17, wherein the tubes have a dimension of 250 μm to 2,000 μm.

27. The radiopaque intervertebral metal implant according to claim 17, wherein the upper plane and the lower plane of the implant have at least 80 tubes per $cm^2$.

28. The radiopaque intervertebral metal implant according to claim 17, wherein the vertical tubes and/or the horizontal tubes don't change their inner diameter on their way through the implant.

29. The radiopaque intervertebral metal implant according to claim 17, wherein the boundary layer is manufactured in one continuous piece.

30. The radiopaque intervertebral metal implant according to claim 17, wherein the implant is selected from the group consisting of cervical cages, thoracic cages, lumbar cages, artificial intervertebral disks and implants for the fusion of natural and artificial vertebrae.

31. The radiopaque intervertebral metal implant according to claim 17, wherein the implant has a ratio of a volume of a material of the implant to a volume of the tubes ranges from 10 vol. %:90 vol. % to 20 vol. %:80 vol. %.

32. The radiopaque intervertebral metal implant according to claim 17, wherein a ratio of a volume of the at least one cavity to an overall volume of the implant within the boundary layer ranges from 1:2 to 1:1.

33. The radiopaque intervertebral metal implant according to claim 17, wherein the metal implant is a titanium implant.

* * * * *